(12) United States Patent
Balk

(10) Patent No.: US 6,673,586 B2
(45) Date of Patent: Jan. 6, 2004

(54) STEROID HORMONE RECEPTOR INTERACTING PROTEIN KINASE

(75) Inventor: Steven Balk, Needham, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 09/765,815

(22) Filed: Jan. 19, 2001

(65) Prior Publication Data

US 2003/0166623 A1 Sep. 4, 2003

Related U.S. Application Data

(60) Provisional application No. 60/176,859, filed on Jan. 19, 2000.

(51) Int. Cl.$^7$ ................................................. C12N 9/12
(52) U.S. Cl. ....................... 435/194; 435/189; 435/193; 424/94.1; 424/94.5; 530/300
(58) Field of Search ................................ 435/189, 193, 435/194; 424/94.1, 94.5; 530/300

(56) References Cited

PUBLICATIONS

Scher, "HER2 In Prostate Cancer—A Viable Target Or Innocent Bystander?," *J. Natl. Cancer Inst.* 92(23):1866–1868 (2000).

Signoretti et al., "Her–2–neu Expression and Progression Toward Androgen Independence In Human Prostate Cancer," *J. Natl. Cancer Inst.* 92(23):1918–1925 (2000).

Yang et al., "Androgen Receptor Specifically Interacts With A Novel p21–activated Kinase, PAK6," *J. Biol. Chem.* 276(18):15345–15353 (2001).

Hong et al., "GRIP1, a Novel Mouse Protein that Serves as a Transcriptional Coactivator in Yeast for the Hormone Binding Domains of Steroid Receptors," *Proc. Natl. Acad. Sci. U.S.A.* 93:4948–4952 (1996).

Polverino et al., "Activation of Mitogen–activated Protein Kinase Cascades by p21–activated Protein Kinases in Cell–Free Extracts of *Xenopus Oocytes*," *J. Biol. Chem.* 270:26067–26070 (1995).

Zenke et al., "Identification of a Central Phosphorylation Site in p21–activated Kinase Regulating Autoinhibition and Kinase Activity," *J. Biol. Chem.* 274:32565–32573 (1999).

*Primary Examiner*—Ponnathapu Achutamurthy
*Assistant Examiner*—Christian L. Fronda
(74) *Attorney, Agent, or Firm*—Clark & Elbing, LLP; Kristina Bieker-Brady

(57) ABSTRACT

The present invention features a novel p21-activated kinase that interacts with steroid hormone receptors, the steroid hormone receptor interacting p21-activated kinase (PAK$_{SI}$). In general, the invention provides methods of inhibiting hormone related cancers. More particularly, the present invention relates to inhibiting prostate cancer and breast cancer. The present invention further provides methods of activating the therapeutic effects of steroid hormone receptors, particularly the estrogen receptor. Alternatively, the present invention provides methods of diagnosing steroid hormone receptor-related diseases.

2 Claims, 11 Drawing Sheets

```
                                                                              88
ggcacgaggcctctcctcagcgcctaagagagaggcccagtgcgggtgaggagtcgcgaggaagaggcggaaggcgccggaaggcacc M   F   R   K   K   K   K   R   P   E   I   S   A   P   Q   N   F   Q   H   R   V   H   T   S   F   D   P   K   E   30
atgttccgcaagaaaaagaagaaacgccctgagatctcagcgccacagaacttccagcaccgtgtccacacctccttcgaccccaaagaa 178
  G   K   F   V   G   L   P   P   Q   W   Q   N   I   L   D   T   L   R   R   P   K   P   V   V   D   P   S   R   I   T   60
ggcaagtttgtgggcctcccccccacaatggcagaacatcctggacacactgcggcgccccaagcccgtggtggacccttcgcgaatcaca 268
  R   V   Q   L   Q   P   M   K   T   V   V   R   G   S   A   M   P   V   D   G   Y   I   S   G   L   L   N   D   I   Q   90
cgggtgcagctccagcccatgaagacagtggtgcggggcagcgcgatgcctgtggatggctacatctcggggctgctcaacgacatccag 378
  K   L   S   V   I   S   S   N   T   L   R   G   R   S   P   T   S   R   R   R   A   Q   S   L   G   L   L   G   D   E   120
aagttgtcagtcatcagctccaacaccctgcgtggccgcagcccaccagccggcggcgggcacagtccctgggctgctggggatgag 468
  H   W   A   T   D   P   D   M   Y   L   Q   S   P   Q   S   E   R   T   D   P   H   G   L   Y   L   S   C   N   G   G   150
cactgggccaccgacccagacatgtacctccagagccccagtctgagcgcactgaccccacggcctctacctcagctgcaacgggggc 558
  T   P   A   G   H   K   Q   M   P   W   P   E   P   Q   S   P   R   V   L   P   N   G   L   A   A   K   A   Q   S   L   180
acaccagcaggccacaagcagatgccgtggcccgagccacagagcccagggtcctgcccaatgggctggctgcaaaggcacagtccctg 648
  G   P   A   E   F   Q   G   A   S   Q   R   C   L   Q   L   G   A   C   L   Q   S   S   P   P   G   A   S   P   P   T   210
ggccccgccgagtttcaggtgcctcgcagcgctgtctgcagctgggtgcctgcctgcagagctccccaccaggagcctcgcccccacg 738
  G   T   N   R   H   G   M   K   A   A   K   H   G   S   E   E   A   R   P   Q   S   C   L   V   G   S   A   T   G   R   240
ggcaccaataggcatggaatgaaggctgccaagctggctctgaggaggcccggccacagtcctgcctggtgggctcagccacaggcagg 828
  P   G   G   E   G   S   P   S   P   K   T   R   E   S   S   L   K   R   R   L   F   R   S   M   F   L   S   T   A   A   270
ccaggtggggaaggcagccctagccctaagacccgggagagcagcctgaagcgcaggctattccgaagcatgttcctgtccactgctgcc 918
  T   A   P   P   S   S   S   K   P   G   P   P   P   Q   S   K   P   N   S   S   F   R   P   P   Q   K   D   N   P   P   300
acagcccctccaagcagcagcaagccaggccctccaccacagagccagcccaactcctcttccgaccgccgcagaaagacaacccccca 1008
  S   L   V   A   K   A   Q   S   L   P   S   D   Q   P   V   G   T   F   S   P   L   T   T   S   D   T   S   S   P   Q   330
agcctggtggccaaggccagtccttgccctcggaccagccggtggggaccttcagccctctgaccacttcggataccagcagccccag 1098
  K   S   L   R   T   A   P   A   T   G   Q   L   P   G   R   S   S   P   A   G   S   P   R   T   W   H   A   Q   I   S   360
aagtccctccgcacagcccccgccacaggccagcttccaggccggtcttccccaggcgggatcccccgcacctggcacgccagatcagc 1188
  T   S   N   L   Y   L   P   Q   D   P   T   V   A   K   G   A   L   A   G   E   D   T   G   V   V   T   H   E   Q   F   390
accagcaacctgtacctgccccaggaccccacggttgccaagggtgcctggctggtgaggacacaggtgttgtgacacatgagcagttc 1278
  K   A   A   L   R   M   V   V   D   Q   G   D   P   R   L   L   L   D   S   Y   V   K   I   G   E   G   S   T   G   I   420
aaggctgcgctcaggatggtggtggaccagggtgaccccccggctgctgctggacagctacgtgaagattggcgagggctccaccggcatc 1368
  V   C   L   A   R   E   K   H   S   G   R   Q   V   A   V   K   M   M   D   L   R   K   Q   Q   R   R   E   L   L   F   450
gtctgcttggcccgggagaagcactcgggccgccaggtggccgtcaagatgatggacctcaggaagcagcagcgcagggagctgctcttc 1458
  N   E   V   V   I   M   R   D   Y   Q   H   F   N   V   V   E   M   Y   K   N   Y   L   V   G   E   E   L   W   V   L   480
aacgaggtggtgatcatgcgggactaccagcacttcaacgtggtggagatgtacaagaactacctggtgggcgaggagctgtgggtgctc 1548
  M   E   F   L   Q   G   G   A   L   T   D   I   V   S   Q   V   R   L   N   E   E   Q   I   A   T   V   C   E   A   V   510
atggagttcctgcaggaggagccctcacagacatcgtctcccaagtcaggctgaatgaggagcagattgccactgtgtgtgaggctgtg 1638
  L   Q   A   L   A   Y   L   H   A   Q   G   V   I   H   R   D   I   K   S   D   S   I   L   L   T   L   D   G   R   V   540
ctgcaggcctggcctacctgcatgctcagggtgtcatccaccgggacatcaagagtgactccatcctgctgaccctcgatggcagggtg 1728
  K   L   S   D   F   G   F   C   A   Q   I   S   K   D   V   P   K   R   K   S   L   V   G   T   P   Y   W   M   A   P   570
aagctctcggacttcggattctgtgctcagatcagcaaagacgtccctaagaggaagtccctggtgggaacccctactggatggctcct 1818
  E   V   I   S   R   S   L   Y   A   T   E   V   D   I   W   S   L   G   I   M   V   I   E   M   V   D   G   E   P   P   600
gaagtgatctccaggtcttttgtatgccactgaggtggatatctggtctctgggcatcatggtgattgagatggtagatggggagccaccg 1908
  Y   F   S   D   S   P   V   Q   A   M   K   R   L   R   D   S   P   P   P   K   L   K   N   S   H   K   V   S   P   V   630
tacttcagtgactcccccagtgcaagccatgaagaggctccgggacagcccccacccaagctgaaaaactctcacaaggtctccccagtg 1998
  L   R   D   F   L   E   R   M   L   V   R   D   P   Q   E   R   A   T   A   Q   E   L   L   D   H   P   F   L   L   Q   660
ctgcgagacttcctggagcggatgctggtgcgggaccccaagagagagccacagcccaggagctcctagaccacccccttcctgctgcag 2088
  T   G   L   P   E   C   L   V   P   L   I   Q   L   Y   R   K   Q   T   S   T   C   *                               681
acagggctacctgagtgcctggtgcccctgatccagctctaccgaaagcagacctccacctgctgagcccaccccaagtatgcctgccac 2178
```

```
PAK1    msnngldiqdkppappmrntstmigvgskdagtlnhgskplppnpeekkkkdrfyrsilp
PAK2    ..d...e.-e.......v.ms..ifst.g..plsa..sl....sv.....prhki-i..fs
PAK3    ..d-...nee......l.mn.nnrdssal------..s.....ma....n..a.l-...f.

CRIB consensus
                    isxpxxfxhxxhvg
PAK1  g--dktnkkkekerpeislpsdfehtihvgfdavtgeftgmpeqwarllqtsnitkseqkkn
PAK2  .t-e.gs...........p...........................l.....
PAK3  .gg.........................................i....l.....
PAK4       mf-g.r.k.v...a..n...rv.t...oheok...l.r..qs.iee.arrpkplvdp
PAKSI      mfr..k.k.....a.qn.q.rv.ts..pke.k.v.l.p..qni.d.-lrrpkpvvdp
```

B

```
                    isxpxxfxhxxhvg
PAK4    mf-gkrkkrveisapsnfehrvhtgfdoheokftglprqwqslieesarrpkplvdp
PAKSI   ..rk.k...p.....q..q.....s..pk.g......p...nildt-l.....v...

PAK4    acitsiqpgapktivrgskgakdgaltllldefenmsvtrsnslrrdspppparargengmp
PAKSI   sr..rv.l.pm..v....ampv..yisg..ndiqkl..is..t..gr..tsrr..qslgllg
```

C

```
                                        gg    g v                a k
PAK1  241-kqkkkpkmsdeeileklrsivsvgdpkkkytrfekigqgasgtvytamdvatgqevaikq
PAK2  220-........t.....m....i.........y....q......f..t...l........
PAK3  239-r.r..s...t.....................................l.i........
PAK4  296-p.repqrv.h.qfraa.qlv.dp...rsyldn.i...e.st.i.ci.tvrss.kl..v.k
PAKSI 378-agedtgvvth.qfkaa..mv.dq...rllldsyv...e.st.i.cl.rekhs.rq..v.m e
PAK1  mnlqqqpkkeliineilvmrenknpnivnyldsylvgdelwvvmeylaggsltdvvtetcmdeg
PAK2  i...k..........k.l......f......f....................a
PAK3  ............................................................
PAK4  .d.rk.qrr..lf..vvi.rdyqhe.v.emyn............f.e..a...i..h.r.n.e
PAKSI .d.rk.qrr..lf..vvi.rdyqhf.v.emykn....e....l..f.q..a...i.sqvrln.e d   n*          dfg
PAK1  qiaavcreclqaleflhsnqvihrdiksdnillgmdgsvkltdfgfcaqitpeqskrstmvgtp
PAK2  ..............a...............v....e..........................
PAK3  .............d..................................................
PAK4  q.....lav.q..sv..aqg.........s...th..r...s...f..qvsk.vpr.ksl....
PAKSI ...t...av....ay..aqg.........s...tl..r...s........skdvp..ksl....

e        d   g
PAK1  ywmapevvtrkaygpkvdiwslgimaiemiegeppylnenplralyliatngtpelqnpeklsa
PAK2  ..................v..................................p
PAK3  ..................v..................................r...
PAK4  ......lis.lp...e........v...vd.....f..p..k.mkm.rd.lp.r.k.lh.v.p
PAKSI ......is.slyate.........v...vd.....fsds.vq.mkrlrdspp.k.k.sh.v.p r                    LxPLxxxA
PAK1  ifrdflnrcldmdvekrgsakellqhqflkiakplssltpliaaakeatknnh
PAK2  .........e.................l..........m.....m.s.r
PAK3  v........e...dr..........p...l............i.....i..ssr
PAK4  slkg..d.l.vr.paq.at.a...k.p..ak.g.pa.iv..mrqnrtr
PAKSI vt....e.m.vr.pqe.at.q....d.p..lqtglpec.v...qlyrkq.st
```

Figure 3

STEROID HORMONE RECEPTOR INTERACTING PROTEIN KINASE

CROSS-REFERENCE TO RELATED APPLICATIONS

This application claims benefit from U.S. Provisional Application No. 60/176,859, filed Jan. 19, 2000, incorporated herein by reference.

STATEMENT AS TO FEDERALLY SPONSORED RESEARCH

The work described herein was funded by NIH Grant R01-CA46457. The United States may have certain rights to the invention.

BACKGROUND OF THE INVENTION

Prostate cancer now ranks as the most prevalent cancer in men. Approximately 160,000 new cases are diagnosed each year; of these new cases, 35,000 will die of metastatic disease. In women, breast cancer kills 45,000 women per year. Steroid hormone receptors and the factors that bind steroid hormone receptors are key players in the maintenance of healthy tissue. Similarly, disregulation of steroid hormone receptors and steroid hormone receptor interacting proteins are important to the development of a wide variety of sex steroid hormone dependent cancers and diseases. Current therapies for such afflictions include surgery (e.g., castration) and chemical treatment (e.g., chemotherapy and hormone ablation therapy).

Androgens in normal prostate epithelium appear to primarily drive differentiation. In contrast, prostate cancer growth is directly androgen stimulated. Thus, one common therapy for the treatment of prostate cancer is androgen ablation therapy, to which most patients respond. Unfortunately, virtually all prostate cancer relapse is clinically androgen independent. Significantly, most androgen independent tumors express high levels of androgen receptor as well as androgen receptor regulated genes, indicating that the androgen receptor is transcriptionally active (van der Kwastet et al., *Int. J. Cancer* 48, 189–193 (1991); Ruizeveld de Winter et al., *Am. J. Pathol.* 144, 735–746 (1994); Taplin et al., *N. Engl. J. Med.* 332, 1393–1398 (1995); Hobisch et al., *Cancer Res.* 55, 3068–3072 (1995); Visakorpi et al., *Nat. Genet.* 9, 401–406 (1995); and Koivisto et al., *Cancer Res.* 57, 314–319 (1997)).

It has been demonstrated that structural changes in the androgen receptor contribute to altered androgen receptor function in primary or androgen independent prostate cancer. Most reports find that the androgen receptor is wild-type in primary androgen dependent prostate cancer, with a few exceptions (Tilley et al., *Clin. Cancer Res.* 2, 277–285 (1996)). In contrast, androgen receptor mutations have been identified in androgen independent prostate cancer (Taplin et al., supra; Culig et al., *Mol. Endocrinol.* 7, 1541–1550 (1993); Suzuki et al., *J. Steroid Biochem. Mol. Biol.* 46, 759–765 (1993); Suzuki et al., *Prostate* 29, 153–158 (1996); and Taplin et al., *Cancer Res.* 59, 2511–2515. (1999)). An analysis of androgen independent prostate cancer from a large number of bone marrow metastases recently showed that androgen receptor ligand binding domain mutations occur primarily in patients treated with the androgen receptor antagonist flutamide (Taplin et al., supra). Importantly, these mutations result in androgen receptors that are strongly stimulated by hydroxyflutamide. Fortunately, patients with these mutations respond to subsequent treatment with bicalutamide, an androgen receptor antagonist that remains active against these mutant androgen receptors (Taplin et al., supra; and Joyce et al., *J. Urol.* 159, 149–153 (1998)).

The above results indicate that additional mechanisms must contribute to androgen independent androgen receptor activity in the majority of patients treated with androgen ablation. For example, androgen receptor function is modulated by a growing list of associated proteins, some of which likely contribute to prostate cancer development or progression. Some of these proteins function as transcriptional co-activators through intrinsic histone acetyltransferase activity, association with CBP/p300, and/or binding to components of the RNA polymerase II complex (Onate et al., *Science* 270, 1354–1357 (1995); Hong et al., *Proc. Natl. Acad. Sci. U.S.A.* 93, 4948–4952 (1996); Voegel et al., *EMBO J.* 15, 3667–3675 (1996); Anzick et al., *Science* 277, 965–968 (1997); Torchia et al., *Curr. Opin. Cell Biol.* 10, 373–383 (1998); Kamei et al., *Cell* 85, 403–414 (1996); and Spencer et al., *Nature* 389, 194–198 (1997)), but their roles and the roles of other androgen receptor associated proteins in prostate cancer remain unclear.

There remains a need for additional therapies for steroid hormone related carcinomas and other steroid hormone-related diseases. A better understanding of androgen receptor-associated cellular communication could greatly facilitate the discovery of drugs and therapeutic methods for the treatment of a broad range of conditions with fewer of the serious and variable side effects prevalent with currently available chemotherapeutic reagents and surgical procedures. Novel agonists and antagonists of the androgen receptor pathway would be invaluable to the field of therapeutics for steroid hormone receptor-related ailments.

SUMMARY OF THE INVENTION

The present invention provides a substantially pure nucleic acid molecule encoding a steroid hormone-interacting p21-activated kinase ($PAK_{SI}$) polypeptide. Preferably, the nucleic acid molecule has the nucleic acid sequence of SEQ ID NO: 1. The invention also provides a substantially pure $PAK_{SI}$ polypeptide. Preferably, the substantially pure $PAK_{SI}$ polypeptide has the amino acid sequence of SEQ ID NO: 2. In a related aspect, the present invention provides a therapeutic composition that includes a $PAK_{SI}$ polypeptide formulated in a physiologically acceptable carrier.

The present invention also provides a method of inhibiting a steroid hormone receptor by administering to an individual a compound that is capable of inhibiting $PAK_{SI}$. The compound may be capable of inhibiting $PAK_{SI}$ expression or $PAK_{SI}$ activity. In a related aspect, the method further provides a method of inhibiting a prostate tumor or a breast tumor by contacting the tumor with a compound that is capable of inhibiting $PAK_{SI}$.

Alternatively, the present invention provides a method of stimulating the beneficial effects of a steroid hormone receptor by administering to an individual a $PAK_{SI}$ agonist. $PAK_{SI}$ agonists can also be used to treat and prevent other steroid hormone-related diseases. In one preferred embodiment, a $PAK_{SI}$ agonist can be administered to an individual to stimulate the therapeutic effects of an estrogen. For example, a $PAK_{SI}$ agonist can be administered to a patient diagnosed with cardiovascular disease to promote vasodilation. Thus, the present invention provides a method of inhibiting cardiovascular disease by administering to an individual a $PAK_{SI}$ agonist.

A particularly valuable aspect of the invention is that it provides for the identification of $PAK_{SI}$ modulatory compounds that may serve as useful therapeutics. Accordingly, the present invention provides a method of determining whether a compound is a $PAK_{SI}$ modulatory compound. The method involves the steps of: (a) providing a cell expressing a $PAK_{SI}$ polypeptide; (b) contacting the cell with a compound; and (c) measuring the expression or enzymatic-activity of $PAK_{SI}$ by the cell. An alteration in the level of the expression or activity indicates that the compound is a $PAK_{SI}$ modulatory compound.

Alternatively, a $PAK_{SI}$ modulatory compound can be identified by the steps of: (a) providing a $PAK_{SI}$ polypeptide or a $PAK_{SI}$ polypeptide fragment having $PAK_{SI}$ enzymatic activity; (b) contacting the $PAK_{SI}$ polypeptide or a $PAK_{SI}$ polypeptide fragment with the compound; and (c) measuring the enzymatic-activity of $PAK_{SI}$. An alteration in the level of the activity of $PAK_{SI}$ indicates that the compound is a $PAK_{SI}$ modulatory compound. The $PAK_{SI}$ polypeptide or a $PAK_{SI}$ polypeptide fragment can be a recombinant polypeptide or polypeptide fragment. This method for the identification of a $PAK_{SI}$ modulatory compound can be performed in vitro.

The present invention further provides a method of diagnosing a mammal, preferably a human, for the presence of prostate cancer. Alternatively, the present invention provides a method of determining whether a mammal has an increased likelihood of developing prostate cancer. The method involves measuring $PAK_{SI}$ gene expression in a sample (e.g., of prostate tissue) from a mammal to determine whether an alteration in $PAK_{SI}$ expression has occurred relative to the $PAK_{SI}$ expression in a sample from an unaffected mammal. An alteration in $PAK_{SI}$ gene expression would be an indication that the mammal has prostate cancer, or an increased likelihood of developing prostate cancer. Alternatively, an alteration in $PAK_{SI}$ gene expression can be measured in a breast tissue sample and compared to a sample taken from an unaffected mammal, to diagnose the presence of breast cancer, or the likelihood of developing breast cancer.

Alternatively, the present invention provides a method of diagnosing a mammal for the presence of prostate cancer, or an increased likelihood of developing prostate cancer, by measuring $PAK_{SI}$ polypeptide enzymatic activity. The method involves (a) collecting a sample from a mammal; (b) measuring the $PAK_{SI}$ enzymatic activity of the sample; and (c) comparing the measured $PAK_{SI}$ enzymatic activity with the relative activity in a sample from an unaffected individual. An alteration in $PAK_{SI}$ enzymatic activity relative to a sample from an unaffected mammal is an indication that the mammal has prostate cancer or an increased likelihood of developing prostate cancer. Of course, this method is also applicable to diagnosis of other steroid hormone receptor-related diseases (e.g., diagnosis of breast cancer).

The present invention also provides a kit for diagnosing a mammal for the presence of a steroid hormone receptor-related disease. The kit may contain, for example, a panel of probes and/or primers specific to the $PAK_{SI}$ gene that can be used to measure the level of $PAK_{SI}$ mRNA expression in a mammal compared to $PAK_{SI}$ expression in a unaffected mammal. Alternatively, the kit may contain assay reagents useful for determining the level of $PAK_{SI}$ enzymatic activity in a sample from a mammal compared to the enzymatic activity of $PAK_{SI}$ in an unaffected mammal.

Finally, the present invention provides methods of treating a patient with a disease characterized by abnormal cell growth or by an abnormal cytoskeleton in a specific cell type by administering a $PAK_{SI}$ modulatory compound to the patient. In one example, the disease characterized by abnormal cell growth is cancer.

Definitions

By "$PAK_{SI}$ gene" is meant a gene encoding a polypeptide having $PAK_{SI}$ steroid hormone receptor binding activity and/or kinase activity. A $PAK_{SI}$ gene is a gene encoding a $PAK_{SI}$ polypeptide having about 60% or greater, or more preferably 70% or greater amino acid sequence identity to the $PAK_{SI}$ polypeptide disclosed herein (SEQ ID NO: 2). For example, the gene may encode human or murine $PAK_{SI}$ polypeptide. A $PAK_{SI}$ gene may also be defined as encoding a polypeptide with at least 50% of the activity of the $PAK_{SI}$ polypeptides described below.

"Polypeptide" means any chain of amino acids regardless of length or post-translational modification (e.g., glycosylation or phosphorylation).

"Substantially identical" means a polypeptide or nucleic acid exhibiting at least 60%, preferably 70%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 or 35 amino acids, and most preferably the full length polypeptide sequence. For nucleic acids, the length of comparison sequences will generally be at least 50 nucleotides, preferably at least 60 nucleotides, more preferably at least 75 or 110 nucleotides, and most preferably the full length nucleic acid sequence.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By "substantially pure nucleic acid" is meant nucleic acid that is free of the genes which, in the naturally-occurring genome of the organism from which the nucleic acid of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (e.g., a cDNA or a genomic or cDNA fragment produced by PCR or restriction endonuclease digestion) independent of other sequences. It also includes recombinant DNA that is part of a hybrid gene encoding additional polypeptide sequence.

"Transformed cell" means a cell into which (or into an ancestor of which) has been introduced, by means of recombinant DNA techniques, a DNA molecule encoding (as used herein) a polypeptide described herein (for example, a $PAK_{SI}$ polypeptide).

"Transformation" means any method for introducing foreign molecules into a cell. For example, molecules may be introduced using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., chloroplasts and mitochondria), bacteria, yeast, fungi, algae, and animal tissue. Alternatively, standard methods of transformation, such as, calcium phosphate precipitation, DEAE dextran, lipofection, and virus-mediated transduction, can be used to transform a cell.

"Purified antibody" means an antibody that is at least 60%, by weight, free from proteins and naturally-occurring organic molecules with which it is naturally associated. Preferably, the preparation is at least 75%, more preferably 90%, and most preferably at least 99%, by weight, antibody, e.g., a $PAK_{SI}$-specific antibody. A purified $PAK_{SI}$ antibody may be obtained, for example, by affinity chromatography using recombinantly-produced $PAK_{SI}$ protein or conserved motif peptides and standard techniques.

By "specifically binds" is meant an antibody that recognizes and binds a protein that is a $PAK_{SI}$-related protein, but that does not substantially recognize and bind other molecules in a sample, e.g., a biological sample that naturally includes other proteins.

By "mutant" is meant different from what normally appears, occurs, or functions. As used herein, the term refers to a nucleic acid sequence which differs from the wild-type nucleic acid sequence. This term also describes a protein encoded by the mutant nucleic acid sequence. The term also means an organism which carries a mutant nucleic acid sequence.

By "biological activity" or "enzymatic activity"0 is meant functional events mediated by a protein. In some embodiments, this includes assaying the amount of $PAK_{SI}$ binding to a steroid hormone receptor, or events assayed by measuring the biochemical events downstream of $PAK_{SI}$ binding a steroid hormone receptor (e.g., an androgen receptor or an estrogen receptor). It also includes interactions of a polypeptide with another polypeptide. The biological activity of $PAK_{SI}$ also includes modulations in cell function, for example, cell growth, cell survival, cell motility, and the structure and function of the cytoskeleton.

By "activating a steroid hormone receptor" is meant, increasing the activity of a steroid hormone receptor above the level of activity in a wild-type cell.

By "activating the therapeutic effects of estrogen" is meant, stimulating the biochemical effect of estrogen (e.g., by stimulating the estrogen receptor itself or stimulating an estrogen-receptor-related biochemical cascade) in a cell by contacting the cell with a compound, e.g., a $PAK_{SI}$ agonist.

By "steroid hormone receptor" is meant an androgen receptor, estrogen receptors (alpha and beta), progesterone receptor, glucocorticoid receptor, and other members of the nuclear receptor family that are regulated by steroid hormone binding. $PAK_{SI}$ may also interact with other nuclear receptors, such as the thyroid hormone receptor or retinoic acid receptors, which bind to ligands other than steroid hormones.

By "cardiovascular disease" is meant, vasoconstriction, atherosclerosis, abnormal angiogenesis, thrombosis, stroke, myocardial infarction, pulmonary embolism, deep-vein thrombosis, transplant-associated vasculopathy, stenosis (e.g., vein graft stenosis or peri-anastomatic prosthetic graft stenosis), restenosis (e.g., restenosis after angioplasty or stent placement, and the like), atheroma, and vasculitis. Cardiovascular disease also refers to vascular conditions that develop after a surgical treatments, such as venous bypass surgery, balloon angioplasty, post-angioplasty of atherosclerotic plaques of both coronary and peripheral arteries, and allo- and xenograft rejection. Alternatively, cardiovascular disease is used to refer to the disease of a patient that has suffered ischemia, reperfusion injury, mechanical injury, immunologic injury, pharmacologic injury of a vessel, or coronary trauma.

By "unaffected mammal" is meant a mammal that does not have a steroid hormone receptor-related disease. For example, the mammal may lack any symptoms of prostate cancer or breast cancer, or would not otherwise benefit from steroid hormone related treatments.

By "modulate," "modulatory," or "modified," as, used herein, is meant increasing or decreasing the biological activity of $PAK_{SI}$. Preferably the biological activity is increased or decreased 50% relative to a control. More preferably, the biological activity is increased or decreased 90% relative to a control. Most preferably, the biological activity is increased or decreased 95% relative to a control.

By "assaying" is meant analyzing the effect of a treatment or exposure, be it chemical or physical, administered to whole animals or cells derived therefrom. The material being analyzed may be an animal, a cell, a tissue, a lysate or extract derived from a cell, or a molecule derived from a cell. The analysis may be, for example, for the purpose of detecting, altered gene expression, altered nucleic acid stability (e.g., mRNA stability), altered protein stability, altered protein levels, or altered protein biological activity. The means for analyzing may include, for example, assaying for $PAK_{SI}$ message or protein, $PAK_{SI}$ kinase activity, or $PAK_{SI}$ steroid hormone receptor binding (i.e., by methods described herein). Such methods include gene analysis to detect alteration (mutation, loss or amplification) or polymorphisms of the $PAK_{SI}$ gene, RNA hybridization (Northern blot or in situ hybridization) for $PAK_{SI}$ message, PCR amplification for $PAK_{SI}$ message, immunological detection of $PAK_{SI}$ using specific antibodies (by immunoblotting, enzyme linked immunoassay, or immunohistochemistry), functional assays including kinase activity, association with other proteins, cell growth, cell survival, cell motility, alterations in the cytoskeleton of a cell, or $PAK_{SI}$ mediated phosphorylation of other proteins.

By "promoter" is meant a minimal sequence sufficient to direct transcription of an operably-linked gene. Also included in the invention are those promoter elements that are sufficient to render promoter-dependent gene expression controllable for cell-type specific, tissue-specific or that are inducible by external signals or agents; such elements may be located in the 5' or 3' regions of the native gene.

"Operably linked" means that a gene and a regulatory sequence (or sequences) are connected in such a way as to permit gene expression when the appropriate molecules (e.g., transcriptional activator proteins) are bound to the regulatory sequence(s).

By "constitutively active," as referred to herein, is meant a nucleic acid sequence that encodes a polypeptide, which when expressed is in an active form at least as often, or more often as the wild-type polypeptide, in a cell in which wild-type polypeptide is naturally expressed. The polypeptide may be in an active form by being phosphorylated, dephosphorylated, cleaved from a propeptide to a peptide, or through a ligand independent mutation.

By "transgenic" is meant any cell or organism that includes a DNA sequence that is inserted by artifice into a cell and becomes part of the genome of the organism which develops from that cell. As used herein, the transgenic organism is generally a transgenic non-human mammalian (e.g., rodents such as rats or mice) or invertebrate (e.g., *Caenorhabditis elegans*), and the DNA (transgene) is inserted by artifice into the genome.

"Transgene" means any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism.

"Conserved region" means any stretch of six or more contiguous amino acids exhibiting at least 30%, preferably 50%, and most preferably 70% amino acid sequence identity between two or more of the $PAK_{SI}$ family members.

"Detectably-labeled" means any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, e.g., fluorescein labeling).

By "antisense" is meant a nucleic acid sequence, regardless of length, that is complementary to the coding strand gene encoding a $PAK_{SI}$-related protein. Preferably, the antisense nucleic acid is capable of decreasing the activity of a $PAK_{SI}$-related protein when present in a cell which normally is modulated by $PAK_{SI}$. Preferably, the decrease is at least 50%, relative to a control, more preferably, 90%, and most preferably, 95–100%.

By "a disease characterized by abnormal growth" is meant a disease that is caused by or results in inappropriately high numbers of cells. This can be a result of inappropriately high levels of cell division, inappropriately low levels of apoptosis, or both. For example, cancers such as lymphoma, leukemia, melanoma, ovarian cancer, breast cancer, pancreatic cancer, prostate cancer, and lung cancer are all examples of disease characterized by abnormal cell growth.

By "a disease characterized by an abnormal cytoskeleton in a specific cell type" is meant a disease in which specific cells have inappropriate levels of cytoskeletal proteins or cytoskeleton associated protein, or in which such proteins are altered (e.g., by phosphorylation or dephosphorlyation). Example of diseases associated with an abnormal cytoskeleton include, for example, Alzheimer's disease, Pick's disease, Charcot-Marie-Tooth disease, Crohn's disease, and dilated cardiomyopathies.

BRIEF DESCRIPTION OF THE DRAWINGS

FIG. 1 depicts the nucleic acid sequence (SEQ ID NO: 1) and amino acid sequence (SEQ ID NO: 2) of $PAK_{SI}$.

FIG. 3 is a drawing that shows the amino acid sequence alignment between $PAK_{SI}$ and other PAK family members (SEQ ID NOS: 3–14), as well as a consensus sequence (SEQ ID NO: 15 and 16).

DESCRIPTION OF THE PREFERRED EMBODIMENTS

The present invention provides a gene encoding a novel human p21 activated kinase (PAK). This novel protein was isolated by its ability to interact with the androgen receptor. Thus, we named the protein $PAK_{SI}$ for steroid hormone receptor interacting p21 activated kinase. Both $PAK_{SI}$ and the androgen receptor are expressed in the human prostate. Since the cloning of the $PAK_{SI}$ gene, we have found that $PAK_{SI}$ also binds to the estrogen receptor. $PAK_{SI}$ may therefore be a key regulatory factor for multiple steroid hormone receptors. This discovery provides valuable information useful for developing therapeutics and diagnostics for steroid hormone receptor-related diseases, such as, for example, prostate cancer, benign prostatic hyperplasia (BPH), and breast cancer, or for diseases such as cardiovascular disease, for which steroid hormones may have a beneficial effect.

Cloning of the $PAK_{SI}$ Gene

The $PAK_{SI}$ gene was cloned by its ability to interact with the androgen receptor. Specifically, $PAK_{SI}$ was identified in a yeast 2-hybrid screen of a human prostate cDNA library using DNA encoding the full length androgen receptor and the androgen receptor DNA binding and ligand binding domains as bait. The interaction of $PAK_{SI}$ with the androgen receptor in yeast was comparable to the interaction of GRIP1 (amino acids 730–1121) (a known androgen receptor binding protein) with the androgen receptor, based upon stimulation of β-galactosidase production (Table 1). These studies indicated that the $PAK_{SI}$/androgen receptor interaction was mediated by the androgen receptor ligand binding domain.

TABLE 1

| Yeast 2-hybrid analysis of $PAK_{SI}$ | | |
| --- | --- | --- |
| Bait | Prey | Fold Induction[a] |
| AR-AT | pACT2-PAK | 1.1 |
| AR-DBD | pACT2-PAK | 0.9 |
| AR-DBD + LBD | pACT2-PAK | 27 |

TABLE 1-continued

Yeast 2-hybrid analysis of $PAK_{SI}$

| Bait | Prey | Fold Induction[a] |
|---|---|---|
| pAS2 vector | pACT2-PAK | 1.2 |
| cortactin | pACT2-PAK | 1.0 |
| AR DBD + LBD | pGAD424-GRIP1 | 5.7 |

[a]Fold indiction of β-galactosidase by DHT

Figure 2:
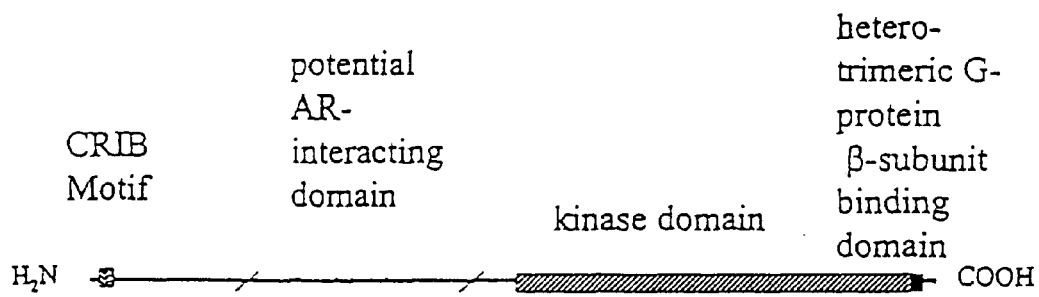
FIG. 2 is a drawing that depicts the structure of $PAK_{SI}$.

A full length cDNA encoding a protein of 681 amino acids (74 kDa) was assembled using a fragment isolated from a testis cDNA library identified in an EST database, in combination with one additional PCR fragment from normal prostate cDNA (FIG. 1). The predicted structure is similar to other PAKs with an amino-terminal CRIB (Cdc42/Rac Interactive Binding) domain, a carboxy serine/threonine kinase domain and a putative heterotrimeric G protein binding domain at the carboxy-terminus (FIG. 2). However, it is noteworthy that $PAK_{SI}$ does not contain a conserved amino-terminal proline rich SH3 region, which appears to mediate interaction with the SH2/SH3 adapter protein Nck and subsequent targeting of PAKs to the plasma membrane (Bokoch et al., *J. Biol. Chem.* 271, 25746–25749 (1996); and Galisteo et al., *J. Biol. Chem.* 271, 20997–21000 (1996)).

PAKs are a family of serine/threonine kinases that bind the active (GTP bound form) of the Rho family small (p21) GTPases, Cdc42 and Rac (Manser et al., *Nature* 367, 40–46 (1994); Martin et al., *EMBO J.* 14, 1970–1978 (1995); and Knaus et al., *Science* 269, 221–223 (1995)), through a conserved amino terminal CRIB domain (Burbelo et al., *J. Biol. Chem.* 270, 29071–29074 (1995)) (FIG. 2). In the unbound state, the CRIB domain negatively regulates PAK carboxy-terminal kinase activity. In the GTP-bound state, GTP-Cdc42 or GTP-Rac binding results in PAK autophosphorylation and activation of kinase activity. Other conserved structural features of previously described PAKs include amino two terminal proline rich SH3-binding motifs and a heterotrimeric G protein β-subunit binding domain at the carboxy-terminal. The homology between $PAK_{SI}$ and other PAK family members is shown in FIG. 3.

The yeast PAK homologue (STE20) activates a MAP kinase analogous to mammalian Raf (Herskowitz, *Cell* 80, 187–197 (1995)) and the three known mammalian PAKs have been reported to similarly activate MAP kinase pathways (Erk, JNK, and p38) in response to activated Cdc42 and/or Rac (Bagrodia et al., *J. Biol. Chem.* 270, 27995–27998 (1995); Frost et al., *EMBO J.* 16, 6426–6438 (1997); Lu et al., *Curr. Biol.* 7, 85–94 (1997); Polverino et al., *J. Biol. Chem.* 270, 26067–26070 (1995); and Zhang et al., *J. Biol. Chem.* 270, 23934–23936 (1995)). Therefore, an androgen receptor-PAK interaction would provide a link between the androgen receptor and other critical signal transduction pathways that have been implicated in prostate cancer development and progression to androgen independence. Our data confirms that the protein we have cloned is a PAK and indicates that it also associates with the estrogen receptor (ER) ligand binding domain. We propose that $PAK_{SI}$ interact with multiple steroid hormone receptors and yield useful therapeutic reagents for treatment of a variety disease conditions.

$PAK_{SI}$ Protein Expression

In general, $PAK_{SI}$ proteins according to the invention, may be produced by transformation of a suitable host cell with all or part of a $PAK_{SI}$-encoding cDNA fragment (e.g., the cDNA described above) in a suitable expression vehicle.

Those skilled in the field of molecular biology will understand that any of a wide variety of commercially available expression systems may be used to provide the recombinant protein. The precise host cell used is not critical to the invention. The $PAK_{SI}$ protein may be produced in a prokaryotic host (e.g., *E. coli*) or in a eukaryotic host (e.g., *Caenorhabditis elegans, Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, (1994)). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., (1985), Supp. (1987)).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (*Mol. Cell Biol.* 5:3610–3616 (1985)).

Alternatively, a $PAK_{SI}$ protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the $PAK_{SI}$ protein is cloned into an expression vector that includes the dihydrofolate reductase (DHFR) gene. Integration of the plasmid and, therefore, the $PAK_{SI}$ protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR− cells, ATCC Accession No. CRL 9096) are among the host cells preferred for DHFR selection of a stably-transfected cell line or DHFR-mediated gene amplification.

Once the recombinant $PAK_{SI}$ protein is expressed, it may be isolated, e.g., using affinity chromatography. In one example, an anti-$PAK_{SI}$ protein antibody (e.g., produced as described herein) may be attached to a column and used to isolate the $PAK_{SI}$ protein. Lysis and fractionation of $PAK_{SI}$ protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier (1980)).

Polypeptides of the invention, particularly short $PAK_{SI}$ protein fragments, can also be produced by chemical synthesis (e.g., by the methods described in *Solid Phase Peptide Synthesis*, 2nd ed., The Pierce Chemical Co., Rockford, Ill. (1984)).

These general techniques of polypeptide expression and purification can also be used to produce and isolate useful $PAK_{SI}$ fragments or analogs (described herein).

Anti-$PAK_{SI}$ Antibodies

To generate $PAK_{SI}$-specific antibodies, a $PAK_{SI}$ coding sequence, or portion thereof, may be expressed as a C-terminal fusion with glutathione S-transferase (GST) (Smith et al., *Gene* 67:31–40 (1988)). The fusion protein may then be purified on glutathione-Sepharose beads, eluted with glutathione, cleaved with thrombin (at the engineered cleavage site), and purified to the degree necessary for immunization of rabbits. Primary immunizations may be carried out with Freund's complete adjuvant and subsequent immunizations with Freund's incomplete adjuvant. Antibody titers may be monitored by Western blot and immunoprecipitation analyses using the thrombin-cleaved $PAK_{SI}$ protein fragment of the GST-$PAK_{SI}$ fusion protein. Immune sera may be affinity purified using CNBr-Sepharose-coupled $PAK_{SI}$ protein. Antiserum specificity may be determined using a panel of unrelated GST proteins (e.g., GSTp53 or Rb) and GST-trypsin (which may be generated by PCR using known sequences).

As an alternate or adjunct immunogen to GST fusion proteins, peptides corresponding to relatively unique hydrophilic regions of $PAK_{SI}$ may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using $PAK_{SI}$ expressed as a GST fusion protein.

Alternatively, monoclonal antibodies may be prepared using the recombinant $PAK_{SI}$ proteins described above and standard hybridoma technology (see, e.g., Kohler et al., *Nature* 256:495 (1975); Kohler et al., *Eur. J. Immunol.* 6:511, (1976); Kohler et al., *Eur. J. Immunol.* 6:292 (1976); Hammerling et al., *In Monoclonal Antibodies and T Cell Hybridomas*, Elsevier, N.Y. (1981); and Ausubel et al., supra). Once produced, monoclonal antibodies are also tested for specific $PAK_{SI}$ recognition by Western blot or immunoprecipitation analysis (by the methods described in Ausubel et al., supra). Antibodies that specifically recognize $PAK_{SI}$ are considered to be useful in the invention; such antibodies may be used, e.g., in an immunoassay to monitor the level of $PAK_{SI}$ produced by a mammalian cell or in a mammal (for example, to determine the amount or location of $PAK_{SI}$).

Preferably, antibodies of the invention are produced using the whole $PAK_{SI}$ polypeptide, but using fragments of the $PAK_{SI}$ potypeptide that lie outside highly conserved regions and appear likely to be antigenic, by criteria such as high frequency of charged residues, may also be used. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

$PAK_{SI}$ is a p21 GTPase Activated Kinase

Figure 4:
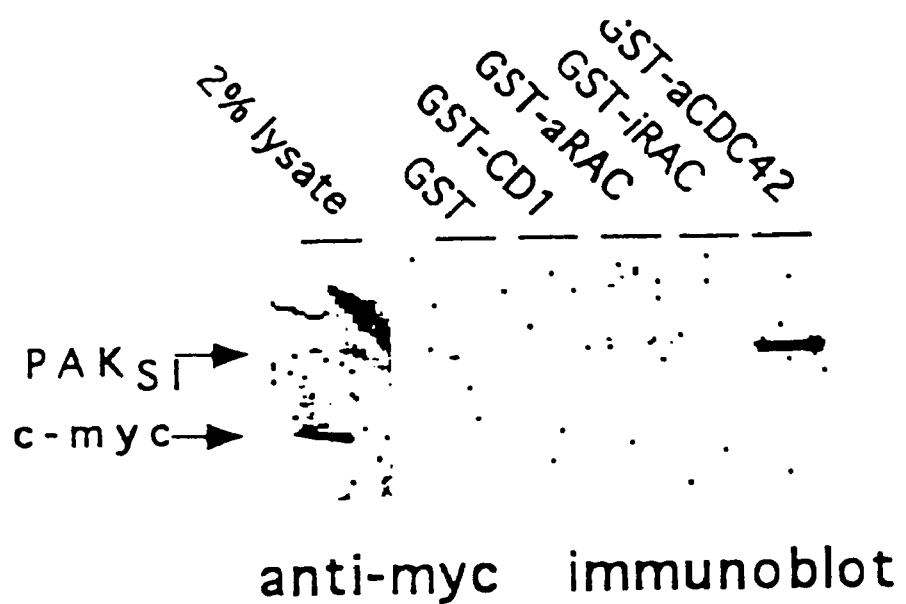
FIG. 4 is a drawing that depicts $PAK_{SI}$ binding to active GST-Cdc42 (ACDC42) and GST-Rac (aRAC). Controls include GST alone and an irrelevant GST-CD1 fusion protein. Whole cell lysate (2%) is shown on the left and positions of the myc-tagged $PAC_{SI}$ and endogenous c-myc are indicated.

Functional studies confirmed that $PAK_{SI}$ is a p21 GTPase activated kinase. First, myc epitope tagged $PAK_{SI}$ was co-transfected into CV1 cells with constitutively active GTPase mutants of Rac and Cdc42, inactive RAC, or control vectors (Rac and Cdc42 vectors kindly provided by L. Cantley, Beth Israel Deaconess Medical Center). $PAK_{SI}$ was then immunoprecipitated using an anti-myc antibody. In vitro kinase assays using myelin basic protein as a phosphorylation substrate confirmed the kinase activity of $PAK_{SI}$ and indicated activation of $PAK_{SI}$ by both Rac and Cdc42. Second, $PAK_{SI}$ binding to GTP-Rac and GTP-Cdc42 was also directly assessed by GST pulldowns experiments. GST-Rac and GST-Cdc42 fusion proteins were first loaded with GTP in vitro (equivalent loading was confirmed by $^{32}$P-GTP binding), and then used to pulldown myc-tagged $PAK_{SI}$ from transfected CV1 cell lysates. FIG. 4 shows $PAK_{SI}$ binding to active Cdc42, but a much weaker association with active Rac, indicating that there may be specificity of $PAK_{SI}$ for Cdc42 at physiological levels in vivo.

Those skilled in the art may investigate whether the androgen or estrogen receptor stimulates $PAK_{SI}$ kinase activity and identify proteins phosphorylated by $PAK_{SI}$ using $PAK_{SI}$ expression vectors and standard methods.

$PAK_{SI}$ Interacts with the Androgen Receptor

Figure 5:
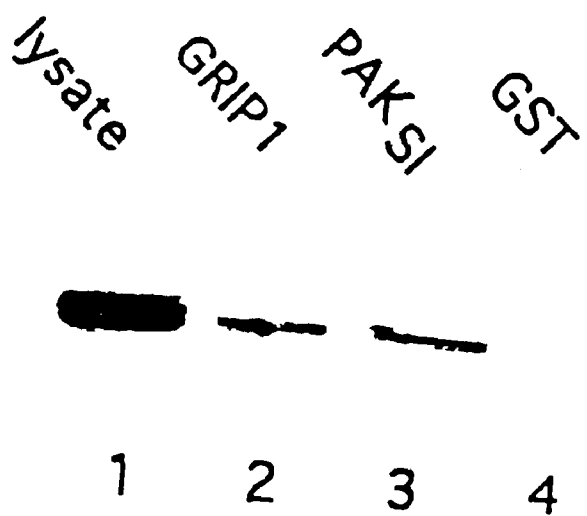
FIG. 5 is photograph of a Western blot that depicts binding of GST-$PAK_{SI}$ to the androgen receptor from LNCaP cells. Lysate (5%, lane 1) and pulldowns with GST-GRIP1, GST-$PAK_{SI}$ (256–682), and GST (lanes 2–4, respectively) were immunoblotted with a polyclonal anti-androgen receptor antibody.
Figure 6:
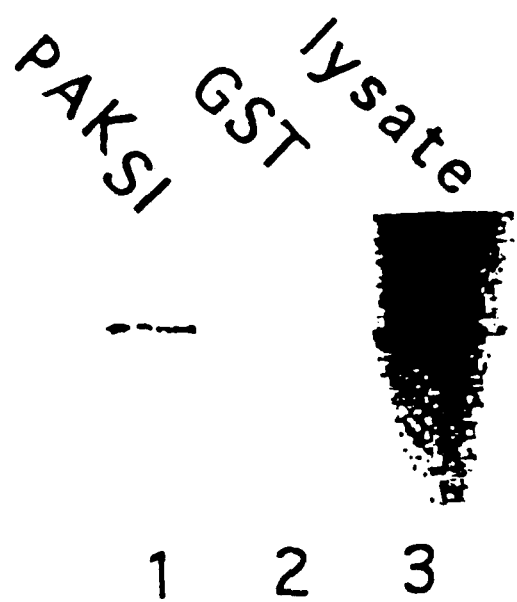
FIG. 6 is a photograph of an autoradiogram that depicts binding of GST-$PAK_{SI}$ to $^{35}S$-labeled in vitro transcribed/translated androgen receptor. Lane 1, GST-$PAK_{SI}$ (256–682); lane 2, GST-GRIP1; lane 3, lysate (5%).

GST pulldown assays were used to confirm the interaction between $PAK_{SI}$ and full length androgen receptor. In FIG. 5, GST-$PAK_{SI}$(256–682) (the region isolated by the yeast 2 hybrid screen which excludes the regulatory CRIB domain), GST-GRIP1(730–1121), and negative control GST fusion proteins were used to pulldown the androgen receptor from LNCaP cells. The $PAK_{SI}$/androgen receptor interaction was detected by anti-androgen receptor immunoblotting, (FIG. 5) or $^{35}$S-labeled in vitro transcribed/translated androgen receptor (FIG. 6). In both cases the results demonstrate specific androgen receptor-$PAK_{SI}$ binding.

Figure 7:
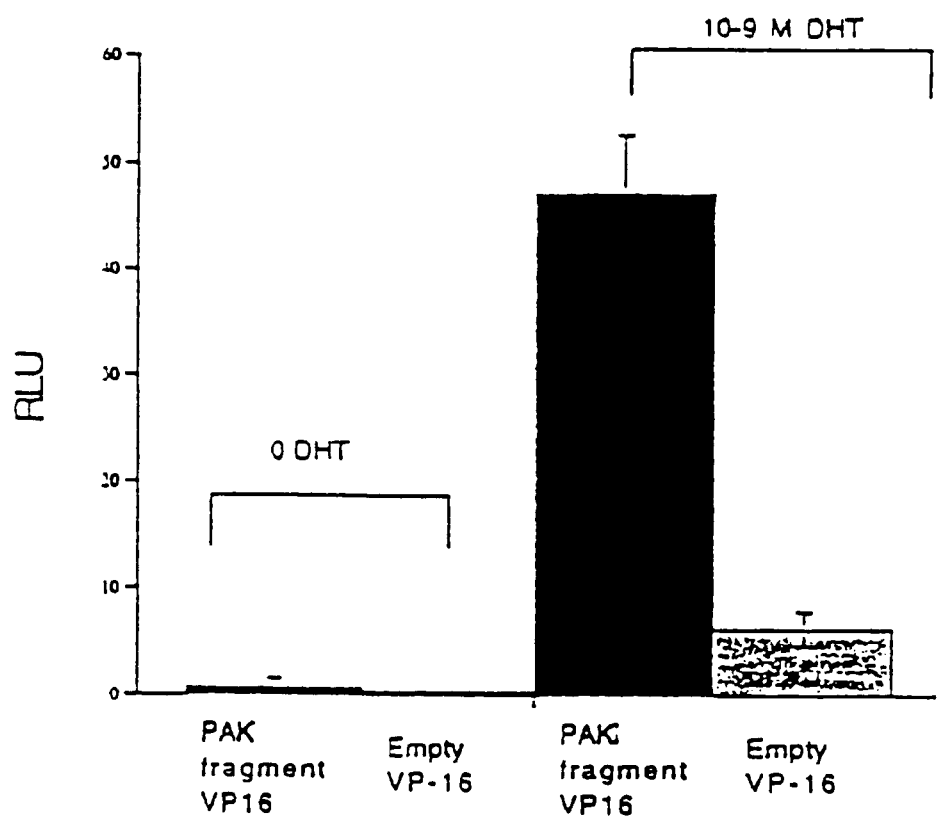
FIG. 7 is a graph that depicts binding of the androgen receptor to $PAK_{SI}$ in vivo. CV1 cells were transfected with the androgen receptor, MMTVLTR-luciferase, β-galactosidase, and the indicated VP16 or VP16-$PAK_{SI}$ expression vectors. Luciferase activity (corrected for control β-galactosidase) plus or minus DHT is shown.

In order to assess whether $PAK_{SI}$ interacts with the androgen receptor in mammalian cells, a VP16-$PAK_{SI}$ (256–682) fusion protein construct was generated. CV1 cells were transfected the androgen receptor, MMTVLTR-luciferase, β-galactosidase control vectors, and the indicated VP16 or VP16-$PAK_{SI}$ expression vectors. Luciferase activity (corrected for control β-galactosidase) was measured in the presence or absence of DHT (FIG. 7). Cotransfection with the VP16-$PAK_{SI}$(256–682) fusion protein resulted in a consistent increase in ligand dependent androgen receptor activity, indicating an in vivo interaction.

It will be appreciated that the domain of $PAK_{SI}$ that mediates androgen receptor binding can be identified by methods well known in the art. We propose herein, without limiting the biochemical mechanism of the invention, that androgen receptor binding by $PAK_{SI}$ is mediated by the region of $PAK_{SI}$ between amino acid 256 (the amino terminal end of the $PAK_{SI}$ isolated form yeast) and amino acid 413 (the beginning of the kinase domain). This can be confirmed by androgen receptor precipitation with a GST-$PAK_{SI}$(256–413) fusion protein. One of ordinary skill in the art can generate a series of deletion mutants using PCR based upon the structure within the $PAK_{SI}$(256–413) fragment. In addition, as described in the assays above, GST pulldown experiments can be used to assess binding of specific domains of $PAK_{SI}$ to the androgen receptor.

Figure 8:
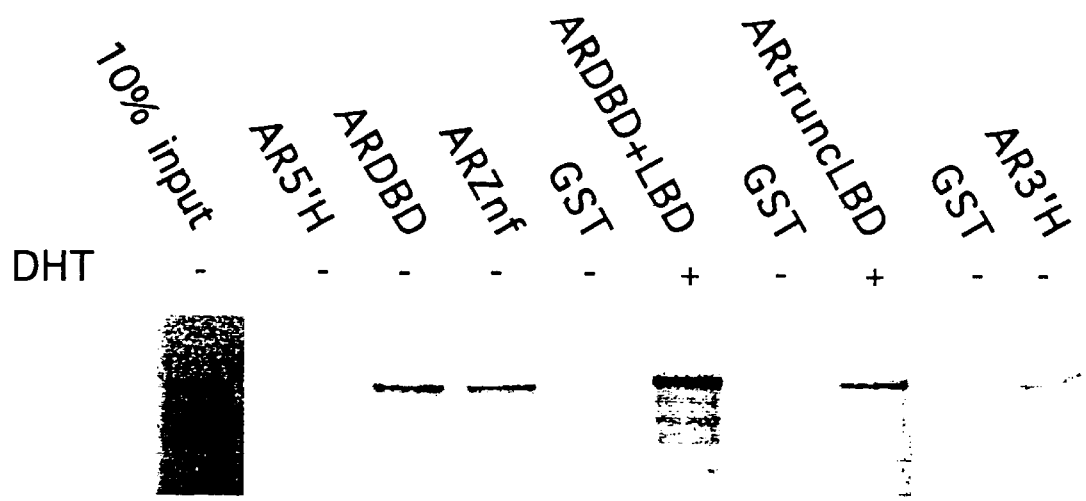
FIG. 8 is a photograph of an autoradiogram showing that $PAK_{SI}$ binds to discrete sites in the androgen receptor DNA binding domain (ARDBD) and the androgen receptor ligand binding domain (ARLBD).

Alternatively, the domain of the androgen receptor that mediates binding to $PAK_{SI}$ can also be identified using similar techniques. For example, FIG. 8 demonstrates that $PAK_{SI}$ binds to discrete sites in the androgen receptor DNA binding domain (ARDBD) and the androgen receptor ligand binding domain (ARLBD). The indicated GST fusion proteins, GST-AR5', GST-ARDBD, GST-ARZ$_{nf}$, (zinc fingers) GST-ARDBD+LBD (ligand-binding domain), GST-AR$_{trunc}$LBD, and GST-AR3'H were used to pulldown $^{35}$S-labeled $PAK_{SI}$, in the presence or absence of DHT. The amino acids included in each of the androgen receptor fusion proteins are: AR5'H 505–566; ARDBD 505–635; $ARZ_{nf}$ 553–635; ARDBD+LBD 505–919; $AR_{trunc}$LBD (truncated LBD) 634–804; AR3'H 634–668. Specific binding was observed with fusion proteins containing the androgen receptor zinc fingers or the 3' hinge region. The strongest binding was observed with the fusion protein containing both (ARDBD+LBD). Thus, two sites in the androgen receptor mediate binding to $PAK_{SI}$, a site in the zinc fingers and a site in the 3' hinge region.

In another preferred embodiment, one skilled in the art can test whether the CRIB domain of $PAK_{SI}$ can block binding of $PAK_{SI}$ to the androgen receptor. The CRIB domains of other PAKs are known to negatively regulate PAK kinase activity and could similarly block androgen receptor binding, which would implicate activated $PAK_{SI}$ (p21 GTPase bound or autophosphorylated) as the androgen receptor binding form. Although this might be addressed by generating full length GST-$PAK_{SI}$, such large GST fusion proteins are not efficiently produced and the amino terminal GST may impair the function of the CRIB domain. Therefore, co-immunoprecipitation experiments using in vitro transcribed/translated androgen receptor and full length (imyc tagged) $PAK_{SI}$ may be assessed and compared to results obtained using CRIB domain deleted $PAK_{SI}$. A control to confirm lack of activation by p21 GTPases in the rabbit reticulocyte lysate could be, for example, an in vitro kinase assay on the PAK immunoprecipitated with anti-myc.

Alternatively, another mechanism by which the potential $PAK_{SI}$/androgen receptor binding inhibitory activity of the CRIB domain of $PAK_{SI}$ may be assessed is by a GST-androgen receptor pulldown of full length or truncated $PAK_{SI}$. It should also be noted that our data indicate that the androgen receptor ligand binding domain is very sensitive to even low concentrations of non-ionic detergents. For this reason, all androgen receptor pulldowns and immunoprecipitations are carried out using extracts generated without detergent. The GST-estrogen receptor (ER)a ligand binding domain fusion protein (kindly provided by M. Brown, Dana Farber Cancer Institute) is a functional alternative to using GST-androgen receptor in such experiments. The skilled artisan is capable of such adjustments to the ionic strength, buffering capacity, etc. to achieve optimal assay conditions.

In another preferred embodiment of this aspect of the invention, the role of Cdc42 may be assessed to determine whether it will compete with or augment $PAK_{SI}$ binding to the androgen receptor. If the CRIB domain blocks $PAK_{SI}$ binding to the androgen receptor, it would suggest that the physiological androgen receptor binding interaction is with activated $PAK_{SI}$. In this case, Cdc42 binding (and/or subsequent $PAK_{SI}$ autophosphorylation) should stimulate androgen receptor binding. Conversely, if the androgen receptor binding interaction is with kinase inactive $PAK_{SI}$, Cdc42 should block androgen receptor binding. These experiments take advantage of the strong binding of full length $PAK_{SI}$ to GST-activated Cdc42 (GTPase deficient and GTP loaded) beads, as described above. In vitro transcribed/translated $PAK_{SI}$ (myc-tagged) may be bound initially to anti-myc or GST-activated Cdc42 beads and the washed beads may then be used to precipitate $^{35}$S-labeled androgen receptor.

In a related aspect, the role of $PAK_{SI}$ autophosphorylation (which occurs in response to Cdc42 binding) may be addressed independently of Cdc42 binding. Using standard methods, $PAK_{SI}$ (myc-tagged) bound to GST-activated Cdc42 beads may be incubated in kinase buffer with cold ATP. Autophosphorylated $PAK_{SI}$ may then be eluted from the beads using EDTA (which disrupts the $Mg^{++}$ dependent GTP binding to Cdc42 and hence $PAK_{SI}$ binding to the Cdc42 beads). $^{35}$S-labeled $PAK_{SI}$/androgen receptor binding may then be assessed by co-immunoprecipitation with anti-myc beads. In this experiment, autophosphorylation and activation of the EDTA eluted $PAK_{SI}$ may be confirmed by standard in vitro kinase assays (Zenke et al., *J. Biol. Chem.* 274, 32565–32573 (1999)).

In another preferred embodiment, the ligand dependency of androgen receptor binding may be evaluated. Androgen receptor-$PAK_{SI}$ binding occurs in the presence of 5α-dihydrotestosterone (DHT), a principal mediator of androgenic activity in the prostate and formed locally in the prostate by the action of testosterone-5α-reductase. The skilled artisan can address whether androgen receptor-$PAK_{SI}$ binding might also occur to unliganded androgen receptor. Such a result would support a role for $PAK_{SI}$ in ligand independent prostate cancer. In these straightforward experiments, GST-$PAK_{SI}$(256–682) may be used to pulldown the androgen receptor (synthesized in vitro or in vivo) with or without DHT or with or without the androgen receptor antagonists hydroxyflutamide bicalutamide. If $PAK_{SI}$ does bind unliganded androgen receptor, it would be important to determine whether binding stimulates androgen receptor release from the HSP90 chaperon complex (possibly through phosphorylation of androgen receptor or some component of the complex).

Figure 9:
FIG. 9 is a photograph of an autoradiogram demonstrating that $PAK_{SI}$ binding to the androgen receptor is ligand independent. $PAK_{SI}$ or control GST fusion proteins (GST alone or GST fused to a portion of the steroid hormone receptor binding protein GRIP) were used to pulldown full length $^{35}S$-labeled androgen receptor).

Indeed, in FIG. 9, we show that $PAK_{SI}$ binding to the androgen receptor can be ligand independent. $PAK_{SI}$ or control GST fusion proteins (GST alone or GST fused to a portion of the steroid hormone receptor binding protein GRIP1) were used to pulldown full length $^{35}$S-labeled androgen receptor. Incubations were carried out in the presence or absence of dihydrotestosterone (DHT, the natural ligand for the androgen receptor, as mentioned above) or bicalutamide (Casodex, Cas, an androgen receptor antagonist). The results demonstrate specific binding of $PAK_{SI}$ to the androgen receptor, which is independent of hormone binding. The binding of $PAK_{SI}$ to the androgen receptor was stronger than the binding of GRIP1, although this may reflect suboptimal folding of the androgen receptor, as GRIP1 binding requires proper ligand induced alignment of several helices in the androgen receptor.

The skilled artisan can also determine whether $PAK_{SI}$ is capable of phosphorylating the androgen receptor. We have observed small mobility shifts in the androgen receptor after pulldown experiments using the active kinase $PAK_{SI}$ (256–682) suggesting that the androgen receptor might be phosphorylated. Androgen receptor phosphorylation may be assessed by standard in vitro kinase assays using $PAK_{SI}$ bound androgen receptor as the substrate. If these experiments confirm androgen receptor phosphorylation by $PAK_{SI}$ in vitro, then co-transfection experiments of androgen receptor and $PAK_{SI}$ (plus or minus activated Cdc42) in combination with $^{32}$P metabolic labeling of the transfected cells may be used to determine whether the androgen receptor is phosphorylated by $PAK_{SI}$ in vivo. Subsequent studies to confirm that $PAK_{SI}$ mediates androgen receptor phosphorylation may employ for example, kinase deficient $PAK_{SI}$ mutants.

It is possible that $PAK_{SI}$ also modulates the transcriptional activity of the androgen receptor. In particular, the skilled artisan may determine whether $PAK_{SI}$ contributes to the apparent ligand independent transcriptional activity of the androgen receptor in androgen independent prostate cancer. Conversely, androgen receptor binding may also modulate $PAK_{SI}$ function.

In order to determine whether $PAK_{SI}$ binding modulates androgen receptor transactivation, a series of standard co-transfections may be carried out using full length androgen receptor and $PAK_{SI}$ expression vectors and an androgen responsive element (ARE) regulated luciferase reporter gene. The skilled artisan can then examine the transcriptional activity of the androgen receptor over a range of DHT concentrations, or in the presence of androgen receptor antagonists (hydroxyflutamide or bicalutamide). The precise reporter gene used for these experiments may be important as the role of $PAK_{SI}$ could be to phosphorylate gene specific transcription factors other than (or in addition to) the androgen receptor, although a variety of gene reporters can be employed in the present assay. Therefore, elements from the PSA gene (both the minimal promoter and a 6.1 kb upstream fragment containing the major PSA enhancer), as well as, for example, the MMTV-LTR may be assessed as reporters. Of course, the skilled artisan will appreciate that any of a variety of reporter systems known in the art can be used in this aspect of the invention (see, Ausubel et al., supra).

We have carried out multiple transfection experiments using the full length $PAK_{SI}$ and the androgen receptor or estrogen receptor. Experiments were carried out using an expression vector encoding full length $PAK_{SI}$. Specifically, CV1 cells were transfected with androgen receptor and control plasmid or $PAK_{SI}$ in conjunction with an androgen regulated luciferase reporter plasmid and a control plasmid (β-galactosidase) for transfection efficiency. Luciferase activity (corrected for control β-galactosidase) is shown. The mean corrected luciferase activity in the samples with androgen receptor and DHT was set at 1 (see, Table 2).

TABLE 2

$PAK_{SI}$ represses androgen receptor transcriptional activity

| Transfected plasmid | DHT | Fold Induction |
|---|---|---|
| androgen receptor | − | 1 |
| androgen receptor | + | 17.2 |
| androgen receptor + $PAK_{SI}$ | − | 1.2 |
| androgen receptor + $PAK_{SI}$ | + | 4.0 |

In the androgen receptor experiments, full length $PAK_{SI}$ repressed androgen receptor transcriptional activity by approximately 4-fold (see Table 2). Similar experiments were carried out using the estrogen receptor, and similar results were observed (Table 3, below). Table 3 shows results obtained when CV1 cells were transfected with the estrogen receptor (ER) and control plasmid or $PAK_{SI}$ in conjunction with an estrogen regulated luciferase reporter plasmid and a control plasmid for transfection efficiency. The mean corrected luciferase activity in the samples with ER and with estradiol (E2) or tamoxifen (Tam) is shown.

TABLE 3

$PAK_{SI}$ inhibition of estrogen receptor

| Transfected Plasmid | Hormone | Fold Induction |
|---|---|---|
| ER | Tam | 2.0 |
| ER | $E_2$ | 25.6 |
| ER + $PAK_{SI}$ | Tam | 0.5 |
| ER + $PAK_{SI}$ | $E_2$ | 3.0 |

This experiment clearly demonstrates that $PAK_{SI}$ represses induction of the estrogen receptor (approximately 8 fold inhibition). These data lend support for androgen receptor/$PAK_{SI}$ and estrogen receptor/$PAK_{SI}$ interactions in vivo.

A second consideration may be whether $PAK_{SI}$ is in an active or inactive state. One aspect of this consideration is the activation state of $PAK_{SI}$. Transfection experiments, such as those described above, may also include constitutively active Cdc42 or Rho-GD1 (an inhibitor of GDP to GTP exchange that should block $PAK_{SI}$ activation by endogenous Rac or Cdc42). Another aspect of this consideration is cell type. Initial experiments may be carried out in, for example, CV1 or PC3 cells, as these are easily transfected and have been used previously to assess androgen receptor function (Fenton et al., Clinical Cancer Research, 3, 1383–1388 (1997)). However, further data on functional interaction between the androgen receptor and $PAK_{SI}$ maybe obtained, from LNCaP cells (which express androgen receptor and can be transfected but at lower efficiency).

It is well known that the transactivation function of the androgen receptor in the absence of androgens may be stimulated by protein kinase A (Nazareth et al., J. Biol. Chem. 271, 19900–19907 (1996); Sadar, J. Biol. Chem. 274, 7777–7783 (1999); and Blok et al., Biochemistry 37, 3850–3857 (1998)) or certain growth factors (Culig et al., Cancer Res. 54, 5474–5478 (1994); and Craft et al., Nat. Med. 5, 280–285 (1999)). The effect of growth factors may be mediated through a MAP kinase pathway (Abreu-Martin, Mol. Cell Biol. 19, 5143–5154 (1999)). Although phosphorylation is presumed to mediate these effects, a role for androgen receptor phosphorylation has not been demonstrated and the mechanisms remain unclear.

Generally, PAKs may be activated by growth factors such as EGF and PDGF (Sadar et al., supra) and have been linked to MAP kinase activation in organisms from yeast through mammalian cells (Herskowitz, supra; Bagrodia et al., supra; Frost et al., supra; Lu et al., supra; Polverino et al., supra; Zhang et al., supra; and Faure et al., J. Biol. Chem. 274, 3573–3579 (1999)), with most evidence supporting a role in activation of the p38 and Jun kinase pathways. We propose that $PAK_{SI}$ may contribute to ligand independent androgen receptor activation by protein kinase A or the EGF receptor family. In a typical experiment, a prostate specific antigen (PSA) 6.1 kb upstream fragment-luciferase reporter gene may be co-transfected with a vectors encoding the androgen receptor and $PAK_{SI}$ (or a kinase deficient $PAK_{SI}$) into cells subsequently maintained in steroid hormone free medium. Cells may then be treated with forskolin (a protein kinase A stimulator). Thereby, the skilled artisan can determine whether $PAK_{SI}$ contributes to ligand independent androgen receptor activation by protein kinase A or the EGF receptor family.

It is also possible that the androgen receptor or estrogen receptor may be a modulator of $PAK_{SI}$ activity. As but one example, the estrogen receptor may be activated by estrogen binding to rapidly stimulate a series; of events, including MAP kinase activation and induction of endothelial nitric oxide synthetase, which are not dependent upon new RNA synthesis (Migliaccio et al., EMBO J. 15, 1292–1300 (1996); Migliaccio et al., EMBO J. 17, 2008–2018 (1998); Castoria et al., EMBO J. 18, 2500–2510 (1999); and Chen et al., J. Clin. Invest. 103, 401–406 (1999)). It has not yet been determined whether the androgen receptor similarly has acute non-transcriptional functions. In any case, these effects may be $PAK_{SI}$ mediated.

We plan to test the hypothesis that the androgen receptor can stimulate (or inhibit) $PAK_{SI}$ kinase activity. The androgen receptor and full length myc-tagged $PAK_{SI}$ may be co-transfected into the appropriate cells and the cells maintained in steroid hormone free medium. The cells may then be pulsed with DHT for 5–30 minutes, followed by anti-myc immunoprecipitation and in vitro kinase assays. Depending upon the results of these initial experiments, baseline levels of $PAK_{SI}$ activation (in the absence of DHT) may be increased by co-transfection with Cdc42 (in order to detect inhibition) or decreased by co-transfection with Rho-GDI (in order to detect activation). If these studies demonstrate androgen receptor modulation of $PAK_{SI}$, potential downstream targets of this pathway may subsequently be identified by methods known in the art and described herein (e.g., pulldown assays).

The PAK family of proteins can regulate diverse cellular functions, including cell growth, cell survival by blocking apoptosis, and cytoskeleton function, the latter contributing to cell motility and other functions of the cytoskeleton (Sells et al., *Curr. Biol.* 7, 202–210 (1997); Dharnawardhane et al., *J. Cell Biol.* 138, 1265–1278 (1997); Abo et al., *EMBO J.* 17, 6527–6540 (1998); Faure et al., supra; Leeuw et al., *Nature* 391, 191–195 (1998); Wang et al., *J. Biol. Chem.* 274, 31641–31647 (1999); Rudel and Bokoch, *Science* 276, 1571–1574 (1997); Lee et al., *Proc. Natl. Acad. Sci. U.S.A.* 94, 13642–13647 (1997); Walter et al., *J. Biol. Chem.* 273, 28733–28739 (1998); and Schurman et al., *Mol. Cell Biol.* 20, 453–461 (2000)). The similarity between $PAK_{SI}$ and other $PAK_{SI}$ indicates that these functions will be similarly regulated by $PAK_{SI}$, either in response to steroid hormones or in response to other $PAK_{SI}$ interacting proteins including activated Cdc42. One skilled in the art can determine if $PAK_{SI}$ regulates cell function by, for example, expressing $PAK_{SI}$ in cells and determining if this expression modulates cell growth, cell motility, cell death, or the cytoskeletal integrity of the cell.

One skilled in the art will further recognize that $PAK_{SI}$ expression may be altered during prostate cancer development or progression. As described above, based on the cDNA cloning of $PAK_{SI}$ from a prostate cDNA library, $PAK_{SI}$ is expressed in normal prostate and testis. We have further demonstrated that the transcript is also expressed in the LNCaP cell line and in a series of metastatic androgen independent prostate cancer samples, based upon RT-PCR our unpublished data. Our next step is to determine whether $PAK_{SI}$ is expressed in particular cell types in normal prostate (e.g., stroma cells, basal cells, or secretory epithelium) or whether its expression changes with prostate cancer.

One approach to determining whether $PAK_{SI}$ expression is altered during prostate cancer development is by use of semi-quantitative RT-PCR. Alternatively, in situ hybridization may be used to determine the level of $PAK_{SI}$ expression in prostate cancer cells. In another preferred embodiment, the skilled artisan may generate a polyclonal, affinity purified antibody and assess $PAK_{SI}$ expression by immunohistochemistry. Alternatively, one may generate a monoclonal antibody to $PAK_{SI}$. Methods of polyclonal and monoclonal antibody preparation are well known in the art and described above (see, for example, Harlow and Lowe, "Antibodies, a Laboratory Manual," Cold Spring Harbor Laboratory, incorporated herein by reference (1988)). Preferably, antibodies to $PAK_{SI}$ are raised in rabbits against unique peptides in the amino terminal and central region of the $PAK_{SI}$ protein, and against a $PAK_{SI}$-GST fusion protein ($PAK_{SI}$ preferably being derived from the central region, excluding the conserved CRIB and kinase domains). Affinity purification and immunohistochemistry may be carried out by standard methods as previously described. In collaboration with Dr. Glenn Bubley (Beth Israel Deaconess Medical Center) we have developed a collection of both frozen and formalin fixed advanced androgen independent prostate cancer samples as well as primary prostate cancer samples that may be used to study $PAK_{SI}$ expression in cancer development.

It will be recognized that the antisera generated to $PAK_{SI}$ can also be used to examine the intracellular distribution of endogenous $PAK_{SI}$ and additionally used in immunoprecipitation experiments. Accordingly, the skilled artisan may assess the intracellular distribution (nuclear versus cytoplasmic) of transfected myc-tagged $PAK_{SI}$, plus or minus the androgen receptor.

$PAK_{SI}$ Binds the Estrogen Receptor

Figure 10:
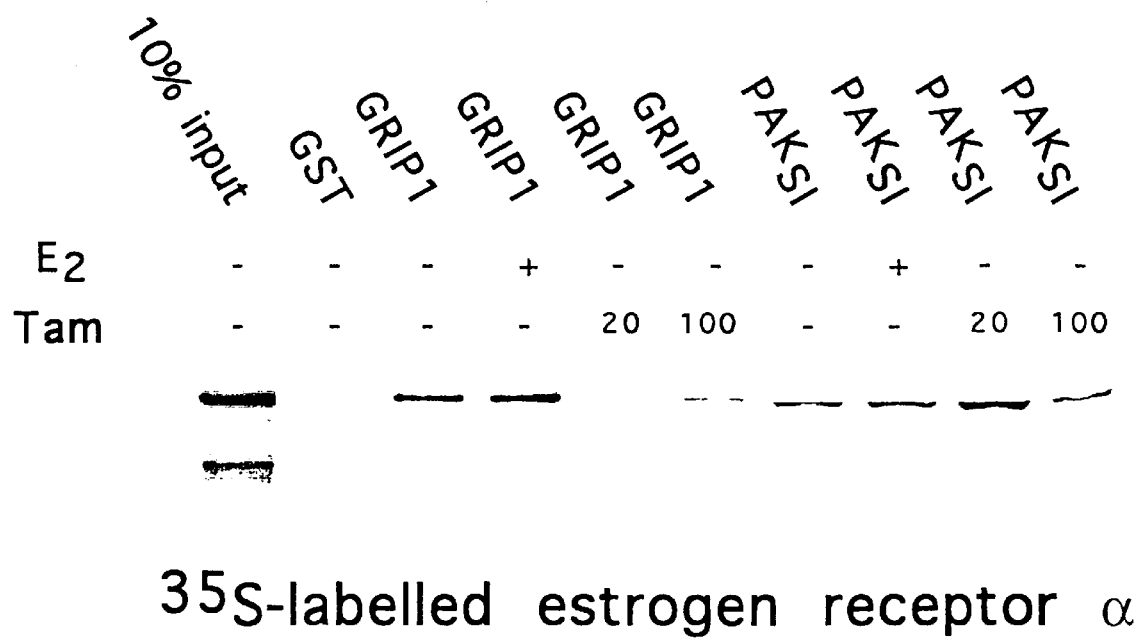
FIG. 10 is a photograph of an autoradiogram demonstrating that $PAK_{SI}$ binds to the estrogen receptor and binding is enhanced by tamoxifen (Tam) and not estradiol ($E_2$), using the control GST fusion proteins of FIG. 9.
Figure 11:
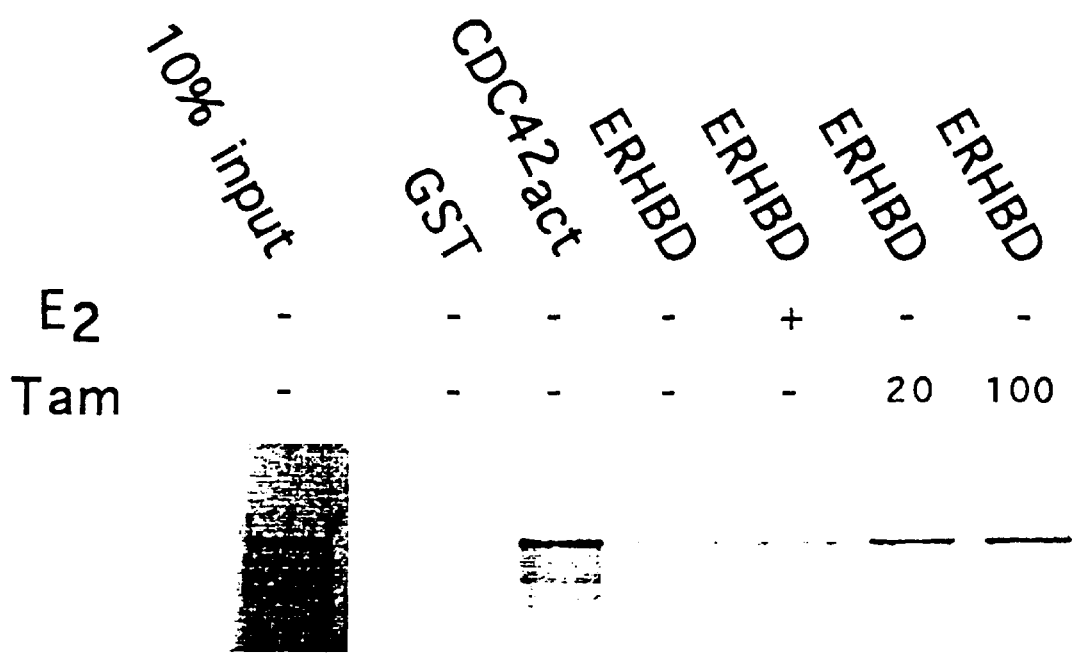
FIG. 11 is a photograph of an autoradiogram demonstrating that $PAK_{SI}$ binds to the estrogen receptor hormone binding domain (ERHBD) and is increased by tamoxifen.

Of course, one of ordinary skill in the art will appreciate that the assays described above to determine the domains mediating androgen receptor-$PAK_{SI}$ interaction, ligand dependence, modulation, and expression can be applied to any steroid hormone receptor to which $PAK_{SI}$ or a $PAK_{SI}$-related protein can bind. For example, as noted above, $PAK_{SI}$ also binds the estrogen receptor. FIGS. 10 and 11 show that $PAK_{SI}$ binds to the estrogen receptor a (ER). In FIG. 10, GST-$PAK_{SI}$ or control GST fusion proteins (GST alone or GST fused to a portion of the steroid hormone receptor binding protein GRIP1) were used to pulldown $^{35}$S-labeled ER. Incubations were carried out in the presence or absence of estradiol ($E_2$, the natural ligand for the estrogen receptor) or tamoxifen (Tam), a partial agonist of the estrogen receptor. As has been shown previously, GRIP1 bound specifically to the estradiol-ligated estrogen receptor (binding in the absence of any hormone likely reflect estrogens in the rabbit reticulocyte lysate used to synthesize the proteins), but not the estrogen receptor incubated with tamoxifen. In contrast, specific ER binding was also observed with $PAK_{SI}$, but in this case binding was enhanced by tamoxifen.

Enhancement of $PAK_{SI}$ binding to the estrogen in the presence of tamoxifen indicates that $PAK_{SI}$ may associate with the ER in patients treated with tamoxifen (and other related partial agonists also called selective estrogen receptor modulators or $SERM_S$) and mediate some important functions of the tamoxifen ligated estrogen receptor. Such functions include stimulation of nitric oxide synthetase (NOS) by endothelial cells, which contributes to the positive effects of estrogen and tamoxifen on the cardiovascular system. Therefore, agents that modulate $PAK_{SI}$ activity could have general use for a number of estrogen-related conditions in addition to prostate and breast disease.

FIG. 11 shows that $PAK_{SI}$ binds to the estrogen receptor hormone binding domain (ERHBD). The indicated GST fusion proteins, GST-Cdc42$_{act}$ and GST-ERHBD, were used to pulldown $^{35}$S-labeled $PAK_{SI}$, in the presence or absence of estradiol or tamoxifen. As in FIG. 10, specific binding to the ER fusion protein (specifically through the ERHBD) was observed and binding was increased by tamoxifen. $PAK_{SI}$ also bound to the activated CDC42 fusion protein.

The estrogen receptor is responsible for carrying out a wide variety of physiological functions. The estrogen receptor plays a key role in the maintenance of normal, healthy breast tissue. However, like the androgen receptor, disregulation of normal estrogen receptor function, for example, via mutation of the estrogen receptor itself or a key estrogen receptor regulatory molecule, can lead to breast cancer. Estrogen receptor-related cancers include endometrial cancer and ovarian cancer. Other estrogen-related conditions include, for example, endometriosis and bone loss.

Various investigators have examined hormonal therapy for breast and endometrial cancer as well as for the treatment of endometriosis and prevention and treatment of bone loss. The most common, currently available approaches for the treatment of breast cancer include chemotherapy (e.g., inhibition of estrogen action and/or formation) and surgical treatment (e.g., removal of the ovaries). The role of estrogen in promoting the growth of estrogen-sensitive breast cancer is well recognized (Lippman, *Semin. Oncol.*, 10 (suppl. 4):11–19 (1983); Sledge and McGuire, *Cancer Res.* 38:61–75 (1984); Wittliff, *Cancer* 53:630–643 (1984), and Poulin and Labrie, *Cancer Res.* 46:4933–4937 (1986)). Estrogens are known to promote the proliferation of normal endometrium. Chronic exposure to estrogens, unopposed by progesterone, can lead to the development of endometrial hyperplasia, which leads to a predisposition to endometrial carcinoma (Lucas, *Obstet. Gynecol. Surv.* 29:507–528 (1974)). The incidence of endometrial cancer increases after menopause, especially in women receiving estrogen therapy, without simultaneous treatment with progestins (Smith et al., *N. Engl. J. Med.* 293:1164–1167 (1975); and Mack et al., *N. Engl. J. Med.* 294:1262–1267 (1976))

A number of actions of the estrogen receptor have no clear mechanism. Perhaps chief among these is the stimulation of nitric oxide production by endothelial cells which results in vasodilation. This effect of the estrogen receptor has been proposed to contribute to the protective effect of estrogens against cardiovascular disease (e.g., atherosclerosis, angiogenesis, stroke, and heart attack) in women.

We propose that steroid hormone receptors, such as the estrogen receptor and the androgen receptor, may mediate one or more of the effects described above by stimulating $PAK_{SI}$. This would imply that a $PAK_{SI}$ agonist might be a very important drug that could deliver many of the positive effects of estrogens without the negative aspects of estrogen therapy. Such a $PAK_{SI}$ agonist would also have the desired beneficial effects in men without inducing the undesirable feminizing effects of estrogen treatment.

As mentioned above, estrogen plays a role in a wide variety of disorders. These include atrophy of the skin and vagina, osteoporosis, premenstrual syndrome, postmenopausal syndrome, ovarian dysgenesis, delayed puberty, sexual infantilism, seborrhea, acne, and male and female infertility.

Estrogen may even play a role in steroid hormone-related diseases in men. Estrogens are produced in men by the testes and by peripheral aromatization of adrenal androgens. Testosterone is the major product of the testis and is converted by 5α-reductase to the more potent androgen, dihydrotestosterone in the prostate (Bruchovsky et al. *J. Biol. Chem.* 243:2012–2021 (1968)). Evidence suggests that estrogens may also play a role in the growth of normal prostate, benign prostatic hypertrophy and prostatic cancer (Mawhinney et al., *Adv. Sex Horm. Res.* 2:41–209 (1976)).

Tissue Distribution of $PAK_{SI}$

To investigate the tissue distribution of $PAK_{SI}$, a human multi-tissue blot containing polyadenylated RNA from multiple human tissue and cells lines was probed. The blot (Human Multiple Tissue Array, Clontech) was probed with a PCR-generated 32P-labeled fragment of $PAK_{SI}$, corresponding to amino acids 115 to 383 (a sequence having no known homology to previously described PAKs or other proteins). Hybridization and washing conditions were carried out according to the manufacturer's directions.

The tissue distribution analysis revealed that $PAK_{SI}$ is expressed strongly in testis and in many areas of the brain, particularly cortical structures. Lower level expression was seen in prostate, thyroid, adrenals, placenta, kidney, esophagus, mammary gland, and heart. There is little or no expression in ovary, uterus, intestine, liver, lung, spleen, thymus, peripheral blood leukocytes, lymph node, or bone marrow.

Methods of Treatment

In preferred embodiments, the present invention provides $PAK_{SI}$ agonists that are capable of specifically stimulating the therapeutic effects of an estrogen (e.g., to increase vasodilation and treat cardiovascular disease). In a related embodiment, the present invention provides $PAK_{SI}$ agonists that are capable of stimulating the therapeutic effects of an androgen. In yet another preferred embodiment, the present invention provides $PAK_{SI}$ agonists that are capable of stimulating the therapeutic effects of a steroid hormone receptor other than the estrogen receptor or the androgen receptor. Such agonists can be used to treat or prevent any of a variety of steroid hormone related diseases.

Thus, the present invention provides methods of activating a steroid hormone receptor by administering to an individual a $PAK_{SI}$ agonist. In a preferred embodiment, the present invention provides a method of activating the therapeutic effects of estrogen by administering to an individual a $PAK_{SI}$ agonist. In an related embodiment, the present invention provides a method of activating the therapeutic effects of an androgen by administering to an individual a $PAK_{SI}$ agonist. In an alternative embodiment, the present invention provides a method of inhibiting cardiovascular disease by administering to an individual a $PAK_{SI}$ agonist having the ability to stimulate the estrogen receptor.

In an another aspect, the present invention provides a method of altering the level of $PAK_{SI}$ in a cell. For example, the present invention provides a method of activating the therapeutic effects of a steroid hormone receptor (i.e., the estrogen receptor) by increasing the level of $PAK_{SI}$ in a cell. One mechanism by which to achieve an increased level of $PAK_{SI}$ in a cell is by administering to a patient a compound capable of increasing the expression or stability of $PAK_{SI}$. In the present embodiment, the compound may be a transcription factor. Alternatively, the therapeutic may be a compound that induces increased expression or stability of the $PAK_{SI}$ protein. An alternative mechanism by which to increase the level of $PAK_{SI}$ in a cell is by expressing a derivative or mutant of the $PAK_{SI}$ protein that is expressed at a higher level or has increased stability within the cell. In another related embodiment a compound may be capable of increasing the activity of $PAK_{SI}$.

In a related embodiment, the present invention similarly provides a method of decreasing the level or activity of $PAK_{SI}$ in a cell (e.g., the estrogen receptor or the androgen receptor) by administering a specific compound to the cell or by expressing a derivative or mutant of the $PAK_{SI}$ protein.

In another preferred embodiment, the present invention provides $PAK_{SI}$ antagonists that are capable of specifically inhibiting the effects of a steroid hormone receptor. Preferably, the steroid hormone receptor is an androgen receptor or an estrogen receptor. Antagonists of the androgen receptor can be used in methods of inhibiting a prostate tumor. Antagonists of the estrogen receptor can be used in methods of inhibiting a breast tumor. Thus, the present invention provides a method of inhibiting a tumor by contacting the tumor, preferably a breast tumor or a prostate tumor, with a compound capable of inhibiting $PAK_{SI}$. Of course, it will be appreciated that the steroid receptor antagonists of the present invention can be used to treat any tumor that has arisen due to disregulation (e.g., increased expression or activity) of a steroid hormone receptor, particularly a sex steroid hormone receptor.

Identification and Administration of Therapeutic Compounds

Isolation of the $PAK_{SI}$ cDNA, as discussed above, facilitates the identification of molecules that modulate $PAK_{SI}$. The present invention provides a method of determining whether a compound is a $PAK_{SI}$ modulatory compound by (a) providing a cell expressing a $PAK_{SI}$ polypeptide; (b)

contacting the cell with a compound; and (c) measuring the expression or enzymatic-activity of $PAK_{SI}$ in the cell. An alteration (i.e., an increase or decrease) in the level of $PAK_{SI}$ expression or activity indicates that the compound is a $PAK_{SI}$ modulatory compound. Methods for carrying out each of these steps are well known in the art. For example, common methods of expressing $PAK_{SI}$ polypeptides in a cell are provided above. Standard protocols and assays for measuring the level of $PAK_{SI}$ expression or activity are also described in detail above.

According to the present invention, an increase or decrease in $PAK_{SI}$ expression can be measured by adding candidate molecules at varying concentrations to the culture medium of cells expression $PAK_{SI}$ mRNA. $PAK_{SI}$ expression is then measured, for example, by standard Northern blot analysis (Ausubel et al., supra) using a $PAK_{SI}$ cDNA (or cDNA fragment) as a hybridization probe. The level of $PAK_{SI}$ expression in the presence of the candidate molecule is compared to the level measured for the same cells in the same culture medium but in the absence of the candidate molecule.

If desired, the effect of candidate modulators on expression may, in the alternative, be measured at the level of $PAK_{SI}$ protein production using the same general approach and standard immunological detection techniques, such as Western blotting or immunoprecipitation with a $PAK_{SI}$-specific antibody.

$PAK_{SI}$ modulatory compounds can also be identified by providing a $PAK_{SI}$ polypeptide or a $PAK_{SI}$ polypeptide fragment having $PAK_{SI}$ enzymatic activity; contacting the $PAK_{SI}$ polypeptide or a $PAK_{SI}$ polypeptide fragment with the compound; and measuring the enzymatic-activity of $PAK_{SI}$. An alteration in the level of the activity of $PAK_{SI}$ indicates that the compound is a $PAK_{SI}$ modulatory compound. The $PAK_{SI}$ polypeptide or a $PAK_{SI}$ polypeptide fragment can be a recombinant polypeptide or polypeptide fragment. This $PAK_{SI}$ modulatory compounds identification method is particularly useful because it can be performed in vitro.

$PAK_{SI}$ candidate modulatory compounds can also be tested for their effects on cell function. For example a candidate modulatory compound can be contacted with a cell that expresses $PAK_{SI}$ or a $PAK_{SI}$ fragment. The cell is then assayed for modulations in cell growth, cell survival, or alterations in the cytoskeleton or cytoskeletal function of the cell, using methods known in the art, compared to a cell that was not contacted with the candidate compound.

Candidate modulators may be purified (or substantially purified) molecules or may be one component of a mixture of compounds (e.g., an extract or supernatant obtained from cells; Ausubel et al., supra). In a mixed compound assay, $PAK_{SI}$ expression is tested against progressively smaller subsets of the candidate compound pool (e.g., produced by standard purification techniques, e.g., HPLC or FPLC) until a single compound or minimal compound mixture is demonstrated to modulate $PAK_{SI}$ expression.

Alternatively, or in addition, candidate compounds may be screened for those which modulate $PAK_{SI}$ steroid hormone receptor binding activity. In this approach, steroid hormone receptor binding in the presence of a candidate compound is compared to steroid hormone receptor binding in its absence, under equivalent conditions. Again, such a screen may begin with a pool of candidate compounds, from which one or more useful modulator compounds are isolated in a step-wise fashion. In addition, as mentioned above, androgen receptor binding may be measured by any of a variety of assays described herein.

Candidate $PAK_{SI}$ modulators include peptide as, well as non-peptide molecules (e.g., peptide or non-peptide molecules found, e.g., in a cell extract (e.g., extracts of plant-, fungal-, prokaryotic-, or animal-based extracts, fermentation broths), mammalian serum, or growth medium on which mammalian cells have been cultured). Libraries of natural compounds in the form of bacterial fungal, plant and animal extracts are commercially available from a number of sources including, but not limited to, Biotics (Sussex, UK), Xenova (Slough, UK) Harbor Branch Oceangraphic Institute (Ft. Pierce, Fla.), and PharmaMar, U.S.A. (Cambridge, Mass.). Alternatively, numerous methods are also available for generating random or directed synthesis (e.g., semi-synthesis or total synthesis) of any number of chemical compounds, including, but not limited to saccharide-, lipid-, peptide-, and nucleic acid-based compounds. For example, numerous means are available for random and directed synthesis of a wide variety of organic compounds and biomolecules, including expression of randomized oligo-nucleotides and oligopeptides. Synthetic compounds as well as existing compounds may also be tested to have $PAK_{SI}$ modulatory activity. Synthetic compound libraries are commercially available, for example, form Bandon Associates (Merrimack, N.H.) and Aldrich Chemical (Milwaukee, Wis.). Known pharmacological agents may be subjected to directed or random chemical, physical, or biochemical modifications, such as acylation, alkylation, esterification, amidification, etc. to produce structural analogs. In addition, natural and synthetically produced libraries may be produced, if desired, according to methods known in the art, for example, by combinatorial-chemistry methods or standard extraction and fractionation methods.

A molecule that promotes a decrease in $PAK_{SI}$ expression or $PAK_{SI}$ steroid hormone receptor binding activity is considered particularly useful in the invention; such a molecule may be used, for example, as a therapeutic to decrease cellular levels of $PAK_{SI}$ and thereby inhibit steroid hormone related cancers. For example, a molecule that decreases the level of $PAK_{SI}$ in a cell may be used in the treatment of tumors. (e.g., a prostate tumor or breast tumor). Alternatively, a molecule that mimics or enhances $PAK_{SI}$ activity may be used in the treatment of cardiovascular disease.

Modulators found to be effective at the level of $PAK_{SI}$ expression or activity may be confirmed as useful in animal models (i.e., the mouse tumor model (Greenberg et al., *Proc. Natl. Acad. Sci. USA*, 92, 3439–3443 (1995)) and, if successful, may be used as therapeutics (e.g., anti-cancer therapeutics).

A $PAK_{SI}$ modulator may be administered with a pharmaceutically-acceptable diluent, carrier, or excipient, in unit dosage form. Conventional pharmaceutical practice may be employed to provide suitable formulations or compositions to administer $PAK_{SI}$ to patients suffering from or presymptomatic for a $PAK_{SI}$-associated disease. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol. Comnpounds may also be administered orally or by anal or vaginal suppository. Therapeutic formulations may be in the form of liquid solutions, creams, gels, lotions, ointments or suspensions, or transdermal patches; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (18th edition), ed. A. Gennaro, Mack Publishing Company, Easton, Pa., incorporated herein by reference (1990). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for $PAK_{SI}$ modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a $PAK_{SI}$ modulatory compound may be combined with more traditional cancer therapies such as surgery, radiation, or chemotherapy.

In light of the above, the present invention provides therapeutic compositions having $PAK_{SI}$ modulatory activity. Alternatively, the present invention also provides a therapeutic composition including the $PAK_{SI}$ polypeptide formulated in a physiologically acceptable carrier.

Diagnostics $PAK_{SI}$ polypeptides and nucleic acid sequences may find diagnostic use in the detection or monitoring of metastatic conditions. In particular, because $PAK_{SI}$ is involved in signaling through steroid hormone receptors and because increased signaling through these receptors can correlate with a poor prognosis for humans with tumors, an alteration in the level of $PAK_{SI}$ production may also provide an indication of the prognosis of the condition. Levels of $PAK_{SI}$ expression may be assayed by any standard technique. For example, its expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY; and Yap and McGee, *Nucl. Acids. Res.* 19:4294, (1991)).

In yet another approach, immunoassays are used to detect or monitor $PAK_{SI}$ protein in a biological sample. $PAK_{SI}$-specific polyclonal or monoclonal antibodies (produced as described above) may be used in any standard immunoassay format (e.g., ELISA, Western blot, or RIA assay) to measure $PAK_{SI}$ polypeptide levels; again comparison is to wild-type $PAK_{SI}$ levels. A decrease in $PAK_{SI}$ production is indicative of an improved prognosis, Examples of immunoassays are described, e.g., in Ausubel et al., supra. Immunohistochemical techniques may also be utilized for $PAK_{SI}$ detection. For example, a tissue sample (for example, a prostate tissue sample) may be obtained from a patient, and a section stained for the presence of $PAK_{SI}$ using an anti-$PAK_{SI}$ antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, (1982); and Ausubel et al. (supra).

Thus, the present invention provides a method of diagnosing a mammal, preferably a human, for the presence of prostate cancer, or the increased likelihood of developing prostate cancer. The method involves, measuring $PAK_{SI}$ gene expression in a sample from a mammal (either directly, i.e., by quantitating the level of $PAK_{SI}$ mRNA, or indirectly, i.e., by quantitating the level of $PAK_{SI}$ protein). An alteration in $PAK_{SI}$ expression relative to a sample from an unaffected mammal is an indication that the mammal has or may develop prostate cancer. One skilled in the art will appreciate that the above described procedure is also applicable to breast cancer, or any other steroid hormone receptor-related cancer.

Alternatively, a mammal can be diagnosed by measuring an alteration in $PAK_{SI}$ activity. The present invention provides a method of diagnosing a mammal for the presence of prostate or breast cancer or an increased likelihood of developing prostate or breast cancer (or other steroid hormone receptor-related disease) by measuring $PAK_{SI}$ polypeptide enzymatic activity in a sample from a mammal. An alteration in $PAK_{SI}$ activity relative to a sample from an unaffected mammal is an indication that the mammal has or may develop prostate or breast cancer.

Gene Therapy

Because the expression level of $PAK_{SI}$ may correlate with steroid hormone receptor activity and tumor prognosis, the $PAK_{SI}$ gene (or a mutant thereof) may also find use in anti-cancer gene therapy. For example, $PAK_{SI}$ polypeptides with alterations that block $PAK_{SI}$ activity may be administered via gene therapy for the treatment of cancer. Alternatively, the beneficial effects of $PAK_{SI}$, for example stimulation of vasodilation, through binding of the estrogen receptor, may encourage use of $PAK_{SI}$ to prevent or treat cardiovascular disease. In particular, a functional $PAK_{SI}$ gene may be introduced into cells at the site of vasoconstriction, or cardiovascular disease.

Retroviral vectors, adenoviral vectors, adeno-associated viral vectors, or other viral vectors with the appropriate tropism for $PAK_{SI}$-expressing cells (for example, cells of the prostate) may be used as gene transfer delivery systems for a therapeutic $PAK_{SI}$ gene construct. Numerous vectors useful for this purpose are generally known (Miller, *Human Gene Therapy* 15–14 (1990); Friedman, *Science* 244:1275–1281 (1989); Eglitis and Anderson, *BioTechniques* 6:608–614 (1988); Tolstoshev and Anderson, *Current Opinion in Biotechnology* 1:55–61 (1990); Sharp, *The Lancet* 337:1277–1278(1991); Cornetta et al., *Nucleic Acid Research and Molecular Biology* 36:311–322 (1987); Anderson, *Science* 226:401–409 (1984); Moen, *Blood Cells* 17:407–416 (1991); Miller and Rosman, *Biotechniques* 7:980–990 (1989); Le Gal La Salle et al., *Science* 259:988–990 (1993); and Johnson, *Chest* 107:77S–83S, (1995)). Retroviral vectors; are particularly well developed and have been used in clinical settings (Rosenberg et al., *N. Engl. J. Med* 323:370 (1990); and Anderson et al., U.S. Pat. No. 5,399,346).

Non-viral approaches may also be employed for the introduction of therapeutic DNA into cells. For example, $PAK_{SI}$ may be introduced into a tumor cell by the techniques of lipofection (Felgner et al., *Proc. Natl. Acad. Sci. USA* 84:7413 (1987); Ono et al., *Neuroscience Lett.* 117:259 (1990); Brigham et al., *Am. J. Med. Sci.* 298:278 (1989); Staubinger and Papahadjopoulos, *Meth. Enz.* 101:512 (1983)); asialorosonucoid-polylysine conjugation (Wu and Wu, *J. Biol. Chem.* 263:14621 (1988); and Wu et al., *J. Biol. Chem.* 264:16985 (1989); or microinjection under surgical conditions (Wolff et al., *Science* 247:1465 (1990)).

For any of the above approaches, the therapeutic $PAK_{SI}$ DNA construct is preferably applied to the site of the malignancy or inflammation and cytotoxic damage (for example, by injection), but may also be applied to tissue in the vicinity of the malignancy or inflammation and cytotoxic damage or even to a blood vessel supplying these areas.

In the gene therapy constructs, $PAK_{SI}$ cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in prostate, breast or vascular endothelial or smooth muscle cells may be used to direct $PAK_{SI}$ expression. Such enhancers include, without limitation, the prostate specific promoters (e.g., from the PSA gene (both the minimal promoter and a 6.1 kb upstream fragment containing the major PSA enhancer)).

Alternatively, if a $PAK_{SI}$ genomic clone is utilized as a therapeutic construct (for example, following its isolation by hybridization with the $PAK_{SI}$ cDNA described above), $PAK_{SI}$ expression is regulated by its cognate regulatory sequences or, if desired, by regulatory sequences derived from a heterologous source, e.g., any of the promoters or regulatory elements described above.

$PAK_{SI}$ gene therapy is accomplished by direct administration of the $PAK_{SI}$ mRNA to a tumor. This mRNA may be produced and isolated by any standard technique, but is most readily produced by in vitro transcription using a $PAK_{SI}$ cDNA under the control of a high efficiency promoter (e.g., the T7 promoter). Administration of $PAK_{SI}$ mRNA to cells (e.g., malignant cells or cells of cardiovascularly diseased tissue) is carried out by any of the methods for direct nucleic acid administration described above.

Ideally, the production of $PAK_{SI}$ protein by any gene therapeutic approach described above, results in a cellular level of $PAK_{SI}$ that is at least equivalent to the normal, cellular level of $PAK_{SI}$ in an unaffected individual. Treatment by any gene therapy approach may be combined with more traditional cancer therapies such as surgery, radiation, or chemotherapy or treatments for cardiovascular disease.

Another therapeutic approach included within the invention involves direct administration of recombinant $PAK_{SI}$ protein, either to the site of a malignancy (for example, by injection) or systemically by any conventional recombinant protein administration technique. The actual dosage of $PAK_{SI}$ depends on a number of factors, including the size and health of the individual patient, but, generally, between 0.1 mg and 100 mg inclusive are administered per day to an adult in any pharmaceutically-acceptable formulation.

The above approaches may also be used to inhibit $PAK_{SI}$ activity by substituting an altered $PAK_{SI}$ polypeptide having $PAK_{SI}$ blocking activity (e.g., have a deletion or insertion at the amino terminus) for the $PAK_{SI}$ polypeptide described above.

Antisense RNA

The gene delivery system described herein can also be used to accommodate antisense technology. Antisense technology is well described in the scientific literature. In certain preferred embodiments, the RNA molecule of any of the gene delivery systems described herein (e.g., adenovirus) encodes an antisense strand of a particular gene of interest. This enables delivery of an antisense molecule to somatic cells for blocking translation of a specific protein. For example, antisense molecules can be delivered that are specific for the $PAK_{SI}$ gene to effectively inhibit translation. Alternatively, antisense molecules can be delivered to tumor cells to prevent translation of specific $PAK_{SI}$ or steroid receptor mRNAs. Ribozyme technology may also be used to incorporate ribozyme catalytic centers into antisense RNAs, creating the ability to site-specifically cleave target RNA substrates (Rossi, *TIBTECH* 13, 301–306 (1995)).

Cloning of Mammalian $PAK_{SI}$ Proteins

In preferred embodiments, the invention features a method of isolating a $PAK_{SI}$ gene or fragment thereof from a cell, involving: (a) providing a sample of cellular DNA; (b) providing a pair of oligonucleotides having sequence homology to a conserved region of a $PAK_{SI}$ gene (for example, oligonucleotides which include fragments of the sequences shown in SEQ ID NO: 1); (c) combining the pair of oligonucleotides with the cellular DNA sample under conditions suitable for polymerase chain reaction-mediated DNA amplification; and (d) isolating the amplified $PAK_{SI}$ gene or fragment thereof. Where a fragment is obtained by PCR, standard library screening techniques may be used to obtain the complete coding sequence. In preferred embodiments, amplification is carried out using a reverse-transcription polymerase chain reaction, for example, the RACE method.

In another preferred embodiment, the invention features a method of identifying a $PAK_{SI}$ gene in a cell, involving: (a) providing a preparation of cellular DNA (for example, from the human genome); (by providing a detectably-labeled DNA sequence having homology to a conserved region or active domain of a $PAK_{SI}$ gene; (c) contacting the preparation of cellular DNA with the detectably-labeled DNA sequence under hybridization conditions providing detection of genes having 50% or greater sequence identity; and (d) identifying a $PAK_{SI}$ gene by its association with the detectable label.

The present invention also provides a method of isolating a $PAK_{SI}$ gene from a recombinant DNA library, involving: (a) providing a recombinant DNA library; (b) contacting the recombinant DNA library with a detectably-labeled gene fragment, produced by standard PCR methods well known in the art, under hybridization conditions providing detection of genes having 50% or greater sequence identity; and (c) isolating a $PAK_{SI}$ gene by its association with the detectable label.

Alternatively, a $PAK_{SI}$ gene may be isolated from a recombinant DNA library, by: (a) providing a recombinant DNA library; (b) contacting the recombinant DNA library with a detectably-labeled $PAK_{SI}$ oligonucleotide under hybridization conditions providing detection of genes having 50% or greater sequence identity; and (c) isolating a PAKS gene by its association with the detectable label.

In yet another preferred embodiment, the invention features a $PAK_{SI}$ gene isolated according to the method involving: (a) providing a sample of cellular DNA; (b) providing a pair of oligonucleotides having sequence homology to a conserved region of a $PAK_{SI}$ gene; (c) combining the pair of oligonucleotides with the cellular DNA sample under conditions suitable for polymerase chain reaction-mediated DNA amplification; and (d) isolating the amplified $PAK_{SI}$ gene or fragment thereof.

Alternatively, a $PAK_{SI}$ gene may be isolated according to the method involving: (a) providing a preparation of cellular DNA; (I)) providing a detectably-labeled DNA sequence having homology to a conserved region of a $PAK_{SI}$ gene; (c) contacting the preparation of DNA with the detectably-labeled DNA sequence under hybridization conditions providing detection of genes having 50% or greater sequence identity; and (d) identifying a $PAK_{SI}$ gene by its association with the detectable label.

In yet another preferred embodiment, a $PAK_{SI}$ gene may be isolated according to the method involving: (a) providing a recombinant DNA library; (b) contacting the recombinant DNA library with a detectably-labeled $PAK_{SI}$ gene fragment, produced by standard methods known in the art, under hybridization conditions providing detection of genes having 50% or greater sequence identity; and (c) isolating a $PAK_{SI}$ gene by its association with the detectable label.

Another method of identifying a $PAK_{SI}$ gene involves: (a) providing a mammalian cell sample; (b) introducing by transformation (e.g. viral, chemical, or mechanical transformation) into the cell sample a candidate $PAK_{SI}$ gene; (c) expressing the candidate $PAK_{SI}$ gene within the cell sample or isolating $PAK_{SI}$ from the tissue sample or protein isolated therefrom; and (d) determining whether the candidate $PAK_{SI}$ gene encodes a protein capable of binding a steroid hormone receptor, preferably the androgen receptor, whereby steroid receptor binding identifies a $PAK_{SI}$ gene.

In a related aspect, the invention features a $PAK_{SI}$ gene isolated according to the method involving: (a) providing a cell sample; (b) introducing by transformation into the cell sample a candidate $PAK_{SI}$ gene; (c) expressing the candidate $PAK_{SI}$ gene within the tissue sample; and (d) determining whether the tissue sample elicits a $PAK_{SI}$ mediated response or decrease thereof, whereby a response identifies a $PAK_{SI}$ gene.

In a final embodiment, the invention features a method of detecting a $PAK_{SI}$ gene in a cell involving: (a) contacting the $PAK_{SI}$ gene or a portion thereof greater than 9 nucleic acids, preferably greater than 18 nucleic acids in length with a preparation of genomic DNA from the cell under hybridization conditions providing detection of DNA sequences having about 50% or greater sequence identity to the conserved DNA sequences of SEQ ID NO: 1, or the sequences which are conserved among $PAK_{SI}$ s relative to other proteins. Preferably, the region of sequence identity used for hybridization is the region of 9 nucleic acids or more encoding the region of highest conservation between known $PAK_{SI}$ family members.

Transgenic Animals

Transgenic animals may be made using standard techniques. For example, the $PAK_{SI}$ gene may be provided using endogenous control sequences or using constitutive, tissue-specific, or inducible regulatory sequences. Transgenic animals lacking functional $PAK_{SI}$ polypeptide may also be made using standard techniques. This may be done by engineering knock-out mutations in the $PAK_{SI}$ gene using DNA sequences provided herein.

Kits

Lastly, the present invention provides a variety of kits containing any of the reagents described herein. For example, in one preferred embodiment, the kit may provide a $PAK_{SI}$ agonist or antagonist for treatment of a steroid hormone-related disorder. In another preferred embodiment, the kit may provide reagents for diagnosing a mammal for the presence of a steroid hormone receptor-related disease, such as prostate cancer, breast cancer, or cardiovascular disease. The kit may contain, for example, a panel of probes and/or primers specific to the $PAK_{SI}$ gene that can be used to measure the level of $PAK_{SI}$ mRNA expression in a mammal compared to $PAK_{SI}$ expression in a unaffected mammal. Alternatively, the kit may contain assay reagents useful in determining the level of $PAK_{SI}$ enzymatic activity in sample from a mammal compared to the enzymatic activity of $PAK_{SI}$ in an unaffected mammal. In yet another preferred embodiment, the kit may contain a gene delivery vehicle encoding a $PAK_{SI}$-related protein or polypeptide. In further preferred embodiments, the kit may provide a means for targeting an antisense RNA of interest to a specific cell type.

What is claimed is:

1. A substantially pure steroid hormone-interacting p21 GTPase activated kinase (PAK$_{SI}$) polypeptide comprising SEQ ID NO: 2.

2. A composition comprising the steroid hormone-interacting p21 GTPase activated kinase (PAK$_{SI}$) polypeptide of claim 1 formulated in a physiologically acceptable carrier.

* * * * *

SEQUENCE LISTING

```
<160> NUMBER OF SEQ ID NOS: 16

<210> SEQ ID NO 1
<211> LENGTH: 2158
<212> TYPE: DNA
<213> ORGANISM: Homo sapiens

<400> SEQUENCE: 1
ggcacgaggc ctctcctcag cgcctaagag agaggcccag tgcgggtgag gagtcgcgag     60
gaagaggcgg aaggcgccgg aaggcaccat gttccgcaag aaaaagaaga aacgccctga    120
gatctcagcg ccacagaact tccagcaccg tgtccacacc tccttcgacc ccaaagaagg    180
caagtttgtg ggcctccccc cacaatggca gaacatcctg gacacactgc ggcgccccaa    240
gcccgtggtg gacccttcgc gaatcacacg ggtgcagctc cagcccatga agacagtggt    300
gcggggcagc gcgatgcctg tggatggcta catctcgggg ctgctcaacg acatccagaa    360
gttgtcagtc atcagctcca acaccctgcg tggccgcagc cccaccagcc ggcggcgggc    420
acagtccctg gggctgctgg gggatgagca ctgggccacc gacccagaca tgtacctcca    480 gagccccag tctgagcgca ctgaccccca cggcctctac ctcagctgca acgggggcac    540
accagcaggc cacaagcaga tgccgtggcc cgagccacag agcccacggg tcctgcccaa    600
tgggctggct gcaaaggcac agtccctggg ccccgccgag tttcagggtg cctcgcagcg    660
ctgtctgcag ctgggtgcct gcctgcagag ctccccacca ggagcctcgc cccccacggg    720
caccaatagg catggaatga aggctgccaa gcatggctct gaggaggccc ggccacagtc    780
```

```
ctgcctggtg ggctcagcca caggcaggcc aggtggggaa ggcagccta gcccaagac      840 ccgggagagc agcctgaagc gcaggctatt ccgaagcatg ttcctgtcca ctgctgccac    900 agccctcca agcagcagca agccaggcc tccaccacag agcaagccca actcctcttt      960
ccgaccgccg cagaaagaca accccccaag cctggtggcc aaggcccagt ccttgccctc    1020
ggaccagccg gtgggacct tcagccctct gaccacttcg gataccagca gcccccagaa    1080
gtccctccgc acagccccgg ccacaggcca gcttccaggc cggtcttccc cagcgggatc    1140
cccccgcacc tggcacgccc agatcagcac cagcaacctg tacctgcccc aggaccccac    1200
ggttgccaag ggtgccctgg ctggtgagga cacaggtgtt gtgacacatg agcagttcaa    1260
ggctgcgctc aggatggtgg tggaccaggg tgaccccggg ctgctgctgg acagctacgt    1320
gaagattggc gagggctcca ccggcatcgt ctgcttggcc cgggagaagc actcgggccg    1380
ccaggtggcc gtcaagatga tggacctcag gaagcagcag cgcagggagc tgctcttcaa    1440
cgaggtggtg atcatgcggg actaccagca cttcaacgtg gtggagatgt acaagaacta    1500
cctggtgggc gaggagctgt gggtgctcat ggagttcctg cagggaggag ccctcacaga    1560
catcgtctcc caagtcaggc tgaatgagga gcagattgcc actgtgtgtg aggctgtgct    1620
gcaggccctg gcctacctgc atgctcaggg tgtcatccac cgggacatca agagtgactc    1680
catcctgctg accctcgatg gcagggtgaa gctctcggac ttcggattct gtgctcagat    1740
cagcaaagac gtccctaaga ggaagtccct ggtgggaacc ccctactgga tggctcctga    1800
agtgatctcc aggtctttgt atgccactga ggtggatatc tggtctctgg gcatcatggt    1860
gattgagatg gtagatgggg agccaccgta cttcagtgac tccccagtgc aagccatgaa    1920
gaggctccgg gacagccccc cacccaagct gaaaaactct cacaaggtct ccccagtgct    1980
gcgagacttc ctggagcgga tgctggtgcg ggaccccca gagagagcca gcccagga     2040 gctcctagac caccccttcc tgctgcagac agggctacct gagtgcctgg tgcccctgat    2100
ccagctctac cgaaagcaga cctccacctg ctgagcccac cccaagtatg cctgccac     2158
```

<210> SEQ ID NO 2
<211> LENGTH: 681
<212> TYPE: PRT
<213> ORGANISM: Homo sapiens

<400> SEQUENCE: 2

```
Met Phe Arg Lys Lys Lys Lys Arg Pro Glu Ile Ser Ala Pro Gln
 1               5                  10                  15

Asn Phe Gln His Arg Val His Thr Ser Phe Asp Pro Lys Glu Gly Lys
                20                  25                  30

Phe Val Gly Leu Pro Pro Gln Trp Gln Asn Ile Leu Asp Thr Leu Arg
            35                  40                  45

Arg Pro Lys Pro Val Val Asp Pro Ser Arg Ile Thr Arg Val Gln Leu
        50                  55                  60

Gln Pro Met Lys Thr Val Val Arg Gly Ser Ala Met Pro Val Asp Gly
    65                  70                  75                  80

Tyr Ile Ser Gly Leu Leu Asn Asp Ile Gln Lys Leu Ser Val Ile Ser
                85                  90                  95

Ser Asn Thr Leu Arg Gly Arg Ser Pro Thr Ser Arg Arg Ala Gln
                100                 105                 110

Ser Leu Gly Leu Leu Gly Asp Glu His Trp Ala Thr Asp Pro Asp Met
        115                 120                 125

Tyr Leu Gln Ser Pro Gln Ser Glu Arg Thr Asp Pro His Gly Leu Tyr
```

```
            130             135             140
Leu Ser Cys Asn Gly Gly Thr Pro Ala Gly His Lys Gln Met Pro Trp
145             150             155             160
Pro Glu Pro Gln Ser Pro Arg Val Leu Pro Asn Gly Leu Ala Ala Lys
                165             170             175
Ala Gln Ser Leu Gly Pro Ala Glu Phe Gln Gly Ala Ser Gln Arg Cys
            180             185             190
Leu Gln Leu Gly Ala Cys Leu Gln Ser Ser Pro Pro Gly Ala Ser Pro
        195             200             205
Pro Thr Gly Thr Asn Arg His Gly Met Lys Ala Ala Lys His Gly Ser
    210             215             220
Glu Glu Ala Arg Pro Gln Ser Cys Leu Val Gly Ser Ala Thr Gly Arg
225             230             235             240
Pro Gly Gly Glu Gly Ser Pro Ser Pro Lys Thr Arg Glu Ser Ser Leu
                245             250             255
Lys Arg Arg Leu Phe Arg Ser Met Phe Leu Ser Thr Ala Ala Thr Ala
            260             265             270
Pro Pro Ser Ser Ser Lys Pro Gly Pro Pro Gln Ser Lys Pro Asn
        275             280             285
Ser Ser Phe Arg Pro Pro Gln Lys Asp Asn Pro Pro Ser Leu Val Ala
    290             295             300
Lys Ala Gln Ser Leu Pro Ser Asp Gln Pro Val Gly Thr Phe Ser Pro
305             310             315             320
Leu Thr Thr Ser Asp Thr Ser Ser Pro Gln Lys Ser Leu Arg Thr Ala
                325             330             335
Pro Ala Thr Gly Gln Leu Pro Gly Arg Ser Ser Pro Ala Gly Ser Pro
            340             345             350
Arg Thr Trp His Ala Gln Ile Ser Thr Ser Asn Leu Tyr Leu Pro Gln
        355             360             365
Asp Pro Thr Val Ala Lys Gly Ala Leu Ala Gly Glu Asp Thr Gly Val
    370             375             380
Val Thr His Glu Gln Phe Lys Ala Ala Leu Arg Met Val Val Asp Gln
385             390             395             400
Gly Asp Pro Arg Leu Leu Leu Asp Ser Tyr Val Lys Ile Gly Glu Gly
                405             410             415
Ser Thr Gly Ile Val Cys Leu Ala Arg Glu Lys His Ser Gly Arg Gln
            420             425             430
Val Ala Val Lys Met Met Asp Leu Arg Lys Gln Gln Arg Arg Glu Leu
        435             440             445
Leu Phe Asn Glu Val Val Ile Met Arg Asp Tyr Gln His Phe Asn Val
    450             455             460
Val Glu Met Tyr Lys Asn Tyr Leu Val Gly Glu Glu Leu Trp Val Leu
465             470             475             480
Met Glu Phe Leu Gln Gly Gly Ala Leu Thr Asp Ile Val Ser Gln Val
                485             490             495
Arg Leu Asn Glu Glu Gln Ile Ala Thr Val Cys Glu Ala Val Leu Gln
            500             505             510
Ala Leu Ala Tyr Leu His Ala Gln Gly Val Ile His Arg Asp Ile Lys
        515             520             525
Ser Asp Ser Ile Leu Leu Thr Leu Asp Gly Arg Val Lys Leu Ser Asp
    530             535             540
Phe Gly Phe Cys Ala Gln Ile Ser Lys Asp Val Pro Lys Arg Lys Ser
545             550             555             560
```

```
Leu Val Gly Thr Pro Tyr Trp Met Ala Pro Glu Val Ile Ser Arg Ser
                565                 570                 575

Leu Tyr Ala Thr Glu Val Asp Ile Trp Ser Leu Gly Ile Met Val Ile
            580                 585                 590

Glu Met Val Asp Gly Glu Pro Pro Tyr Phe Ser Asp Ser Pro Val Gln
            595                 600             605

Ala Met Lys Arg Leu Arg Asp Ser Pro Pro Lys Leu Lys Asn Ser
        610              615             620

His Lys Val Ser Pro Val Leu Arg Asp Phe Leu Glu Arg Met Leu Val
625                 630                 635                 640

Arg Asp Pro Gln Glu Arg Ala Thr Ala Gln Glu Leu Leu Asp His Pro
                645                 650                 655

Phe Leu Leu Gln Thr Gly Leu Pro Glu Cys Leu Val Pro Leu Ile Gln
                660                 665             670

Leu Tyr Arg Lys Gln Thr Ser Thr Cys
            675                 680

<210> SEQ ID NO 3
<211> LENGTH: 120
<212> TYPE: PRT
<213> ORGANISM: Homo sapiens

<400> SEQUENCE: 3

Met Ser Asn Asn Gly Leu Asp Ile Gln Asp Lys Pro Pro Ala Pro Pro
1               5                   10                  15

Met Arg Asn Thr Ser Thr Met Ile Gly Val Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65              70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn
        115                 120

<210> SEQ ID NO 4
<211> LENGTH: 33
<212> TYPE: PRT
<213> ORGANISM: Homo sapiens

<400> SEQUENCE: 4

Asp Glu Glu Val Met Ser Ile Phe Ser Thr Gly Pro Leu Ser Ala Ser
1               5                   10                  15

Leu Ser Val Pro Arg His Lys Ile Ile Phe Ser Thr Glu Gly Ser Pro
            20                  25                  30

Leu

<210> SEQ ID NO 5
<211> LENGTH: 26
<212> TYPE: PRT
<213> ORGANISM: Homo sapiens
```

```
<400> SEQUENCE: 5

Asp Asn Glu Glu Leu Met Asn Asn Arg Asp Ser Ser Ala Leu Ser
 1               5                  10                  15

Met Ala Asn Ala Leu Phe Gly Gly Ile Leu
            20                  25

<210> SEQ ID NO 6
<211> LENGTH: 33
<212> TYPE: PRT
<213> ORGANISM: Homo sapiens

<400> SEQUENCE: 6

Met Phe Gly Arg Lys Val Ala Asn Arg Val Thr Gln His Glu Gln Lys
 1               5                  10                  15

Leu Arg Gln Ser Ile Glu Glu Ala Arg Arg Pro Lys Pro Leu Val Asp
            20                  25                  30

Pro

<210> SEQ ID NO 7
<211> LENGTH: 34
<212> TYPE: PRT
<213> ORGANISM: Homo sapiens

<400> SEQUENCE: 7

Met Phe Arg Lys Lys Ala Gln Asn Gln Arg Val Thr Ser Pro Lys Glu
 1               5                  10                  15

Lys Val Leu Pro Gln Asn Ile Asp Leu Arg Arg Pro Lys Pro Val Val
            20                  25                  30

Asp Pro

<210> SEQ ID NO 8
<211> LENGTH: 118
<212> TYPE: PRT
<213> ORGANISM: Homo sapiens

<400> SEQUENCE: 8

Met Phe Gly Lys Arg Lys Lys Arg Val Glu Ile Ser Ala Pro Ser Asn
 1               5                  10                  15

Phe Glu His Arg Val His Thr Gly Phe Asp Gln His Glu Gln Lys Phe
            20                  25                  30

Thr Gly Leu Pro Arg Gln Trp Gln Ser Leu Ile Glu Glu Ser Ala Arg
        35                  40                  45

Arg Pro Lys Pro Leu Val Asp Pro Ala Cys Ile Thr Ser Ile Gln Pro
    50                  55                  60

Gly Ala Pro Lys Thr Ile Val Arg Gly Ser Lys Gly Ala Lys Asp Gly
65                  70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
                100                 105                 110

Gln Glu Asn Gly Met Pro
            115

<210> SEQ ID NO 9
<211> LENGTH: 56
<212> TYPE: PRT
<213> ORGANISM: Homo sapiens

<400> SEQUENCE: 9
```

```
Arg Lys Lys Pro Gln Gln Ser Pro Lys Gly Pro Asn Ile Leu Asp Thr
 1               5                  10                  15

Leu Val Ser Arg Arg Val Leu Pro Met Val Ala Met Pro Val Tyr Ile
             20                  25                  30

Ser Gly Asn Asp Ile Gln Lys Leu Ile Ser Thr Gly Arg Thr Ser Arg
             35                  40                  45

Arg Gln Ser Leu Gly Leu Leu Gly
         50                  55

<210> SEQ ID NO 10
<211> LENGTH: 305
<212> TYPE: PRT
<213> ORGANISM: Homo sapiens

<400> SEQUENCE: 10

Lys Gln Lys Lys Pro Lys Met Ser Asp Glu Glu Ile Leu Glu Lys
 1               5                  10                  15

Leu Arg Ser Ile Val Ser Val Gly Asp Pro Lys Lys Lys Tyr Thr Arg
             20                  25                  30

Phe Glu Lys Ile Gly Gln Gly Ala Ser Gly Thr Val Tyr Thr Ala Met
             35                  40                  45

Asp Val Ala Thr Gly Gln Glu Val Ala Ile Lys Gln Met Asn Leu Gln
             50                  55                  60

Gln Gln Pro Lys Lys Glu Leu Ile Ile Asn Glu Ile Leu Val Met Arg
65                   70                  75                  80

Glu Asn Lys Asn Pro Asn Ile Val Asn Tyr Leu Asp Ser Tyr Leu Val
                 85                  90                  95

Gly Asp Glu Leu Trp Val Val Met Glu Tyr Leu Ala Gly Gly Ser Leu
                100                 105                 110

Thr Asp Val Val Thr Glu Thr Cys Met Asp Glu Gly Gln Ile Ala Ala
            115                 120                 125

Val Cys Arg Glu Cys Leu Gln Ala Leu Glu Phe Leu His Ser Asn Gln
130                 135                 140

Val Ile His Arg Asp Ile Lys Ser Asp Asn Ile Leu Leu Gly Met Asp
145                 150                 155                 160

Gly Ser Val Lys Leu Thr Asp Phe Gly Phe Cys Ala Gln Ile Thr Pro
                165                 170                 175

Glu Gln Ser Lys Arg Ser Thr Met Val Gly Thr Pro Tyr Trp Met Ala
                180                 185                 190

Pro Glu Val Val Thr Arg Lys Ala Tyr Gly Pro Lys Val Asp Ile Trp
                195                 200                 205

Ser Leu Gly Ile Met Ala Ile Glu Met Ile Glu Gly Glu Pro Pro Tyr
210                 215                 220

Leu Asn Glu Asn Pro Leu Arg Ala Leu Tyr Leu Ile Ala Thr Asn Gly
225                 230                 235                 240

Thr Pro Glu Leu Gln Asn Pro Glu Lys Leu Ser Ala Ile Phe Arg Asp
                245                 250                 255

Phe Leu Asn Arg Cys Leu Asp Met Asp Val Glu Lys Arg Gly Ser Ala
                260                 265                 270

Lys Glu Leu Leu Gln His Gln Phe Leu Lys Ile Ala Lys Pro Leu Ser
                275                 280                 285

Ser Leu Thr Pro Leu Ile Ala Ala Ala Lys Glu Ala Thr Lys Asn Asn
            290                 295                 300

His
```

<210> SEQ ID NO 11
<211> LENGTH: 27
<212> TYPE: PRT
<213> ORGANISM: Homo sapiens

<400> SEQUENCE: 11

Thr Met Thr Ile Tyr Gln Phe Thr Leu Ile Lys Lys Leu Phe Phe Ala
1               5                   10                  15

Ala Val Glu Val Pro Glu Leu Met Met Ser Arg
            20                  25

<210> SEQ ID NO 12
<211> LENGTH: 20
<212> TYPE: PRT
<213> ORGANISM: Homo sapiens

<400> SEQUENCE: 12

Arg Arg Ser Thr Leu Ile Asp Val Arg Val Glu Asp Arg Pro Leu Ile
1               5                   10                  15

Ile Ser Ser Arg
            20

<210> SEQ ID NO 13
<211> LENGTH: 151
<212> TYPE: PRT
<213> ORGANISM: Homo sapiens

<400> SEQUENCE: 13

Pro Arg Glu Pro Gln Arg Val His Gln Phe Arg Ala Ala Gln Leu Val
1               5                   10                  15

Asp Pro Arg Ser Tyr Leu Asp Asn Ile Glu Ser Thr Ile Cys Ile Thr
            20                  25                  30

Val Arg Ser Ser Lys Leu Val Lys Asp Arg Lys Gln Arg Arg Leu Phe
        35                  40                  45

Val Val Ile Arg Asp Tyr Gln His Glu Val Glu Met Tyr Asn Phe Glu
    50                  55                  60

Ala Ile His Arg Asn Glu Gln Leu Ala Val Gln Ser Val Ala Gln Gly
65                  70                  75                  80

Ser Thr His Arg Ser Phe Gln Val Ser Lys Val Pro Arg Lys Ser Leu
                85                  90                  95

Leu Ile Ser Leu Pro Glu Val Val Asp Phe Pro Lys Met Lys Met Arg
            100                 105                 110

Asp Leu Pro Arg Lys Leu His Val Pro Ser Leu Lys Gly Asp Leu Val
        115                 120                 125

Arg Pro Ala Gln Ala Thr Ala Lys Pro Ala Lys Gly Pro Ala Ile Val
    130                 135                 140

Met Arg Gln Asn Arg Thr Arg
145                 150

<210> SEQ ID NO 14
<211> LENGTH: 162
<212> TYPE: PRT
<213> ORGANISM: Homo sapiens

<400> SEQUENCE: 14

Ala Gly Glu Asp Thr Gly Val Val Thr His Gln Phe Lys Ala Ala Met
1               5                   10                  15

```
-continued

Val Asp Gln Arg Leu Leu Asp Ser Tyr Val Glu Ser Thr Ile Cys
            20                  25                  30

Leu Arg Glu Lys His Ser Arg Gln Val Met Asp Arg Lys Gln Arg Arg
            35                  40                  45

Leu Phe Val Val Ile Arg Asp Tyr Gln His Phe Val Glu Met Tyr Lys
            50                  55                  60

Asn Glu Leu Phe Gln Ala Ile Ser Gln Val Arg Leu Asn Glu Thr Ala
 65                  70                  75                  80

Val Ala Tyr Ala Gln Gly Ser Thr Leu Arg Ser Ser Lys Asp Val Pro
                85                  90                  95

Lys Ser Leu Ile Ser Ser Leu Tyr Ala Thr Glu Val Val Asp Phe Ser
                100                 105                 110

Asp Ser Val Gln Met Lys Arg Leu Arg Asp Ser Pro Pro Lys Lys Ser
            115                 120                 125

His Val Pro Val Thr Glu Met Val Arg Pro Gln Glu Ala Thr Gln Asp
            130                 135                 140

Pro Leu Gln Thr Gly Leu Pro Glu Cys Val Gln Leu Tyr Arg Lys Gln
145                 150                 155                 160

Ser Thr

<210> SEQ ID NO 15
<211> LENGTH: 14
<212> TYPE: PRT
<213> ORGANISM: Homo sapiens
<220> FEATURE:
<221> NAME/KEY: VARIANT
<222> LOCATION: 5,6,8,10,11
<223> OTHER INFORMATION: Xaa = Any Amino Acid

<400> SEQUENCE: 15

Ile Ser Xaa Pro Xaa Xaa Phe Xaa His Xaa Xaa His Val Gly
 1               5                  10

<210> SEQ ID NO 16
<211> LENGTH: 24
<212> TYPE: PRT
<213> ORGANISM: Homo sapiens
<220> FEATURE:
<221> NAME/KEY: VARIANT
<222> LOCATION: 18,21,22,23
<223> OTHER INFORMATION: Xaa = Any Amino Acid

<400> SEQUENCE: 16

Gly Gly Gly Val Ala Lys Glu Asp Asn Asp Phe Gly Glu Asp Gly Arg
 1               5                  10                  15

Leu Xaa Pro Leu Xaa Xaa Xaa Ala
            20
```